(12) United States Patent
Wassel et al.

(10) Patent No.: US 8,968,775 B2
(45) Date of Patent: Mar. 3, 2015

(54) MICROEMULSION TOPICAL DELIVERY PLATFORM

(71) Applicant: EyeCRO, LLC, Oklahoma City, OK (US)

(72) Inventors: Ronald A. Wassel, Guthrie, OK (US); Fadee G. Mondalek, Oklahoma City, OK (US); Rafal A. Farjo, Oklahoma City, OK (US); Alexander B. Quiambao, Oklahoma City, OK (US); Didier J. Nuño, Oklahoma City, OK (US)

(73) Assignee: EyeCRO, LLC, Oklahoma City, OK (US)

( * ) Notice: Subject to any disclaimer, the term of this patent is extended or adjusted under 35 U.S.C. 154(b) by 0 days.

(21) Appl. No.: 14/212,675

(22) Filed: Mar. 14, 2014

(65) Prior Publication Data

US 2014/0275263 A1   Sep. 18, 2014

Related U.S. Application Data

(60) Provisional application No. 61/784,005, filed on Mar. 14, 2013.

(51) Int. Cl.
| | |
|---|---|
| *A61K 9/66* | (2006.01) |
| *A61K 31/19* | (2006.01) |
| *A61K 47/00* | (2006.01) |
| *A61K 47/34* | (2006.01) |
| *A61K 9/00* | (2006.01) |
| *A61K 47/14* | (2006.01) |
| *A61K 31/192* | (2006.01) |
| *A61K 31/122* | (2006.01) |
| *A61K 9/107* | (2006.01) |
| *A61K 31/216* | (2006.01) |

(52) U.S. Cl.
CPC .............. *A61K 47/34* (2013.01); *A61K 9/0048* (2013.01); *A61K 47/14* (2013.01); *A61K 31/192* (2013.01); *A61K 31/122* (2013.01); *A61K 9/1075* (2013.01); *A61K 31/216* (2013.01)
USPC ........... 424/455; 514/569; 514/571; 514/772; 514/785

(58) Field of Classification Search
CPC . A61K 31/122; A61K 31/192; A61K 31/216; A61K 47/14; A61K 47/34; A61K 9/0048; A61K 9/1075; A61K 9/4858; A61K 31/19; A61K 8/37; A61K 9/0014; A61K 33/00; A61K 9/007
USPC ........... 424/451, 455; 514/569, 571, 772, 785
See application file for complete search history.

(56) References Cited

U.S. PATENT DOCUMENTS

| | | | |
|---|---|---|---|
| 7,569,612 B1 * | 8/2009 | Arnold et al. ................. | 514/687 |
| 8,058,316 B2 * | 11/2011 | Farjo ............................. | 514/732 |
| 2005/0153927 A1 * | 7/2005 | Clark et al. ..................... | 514/49 |
| 2009/0232743 A1 * | 9/2009 | Varanasi et al. ................ | 424/45 |
| 2012/0207682 A1 | 8/2012 | Ashton | |

FOREIGN PATENT DOCUMENTS

WO   WO-2013/049621 A1   4/2013

OTHER PUBLICATIONS

Ammar, H. O. et al., "Nanoemulsion as a Potential Ophthalmic Delivery System for Dorzolamide Hydrochloride", *AAPS PharmSciTech*, 10(3):808-819 (Cairo, Egypt, Jun. 18, 2009).
Anonymous, "Microemulsion", *Wikipedia*, pp. 1-11 (Mar. 15, 2014; downloaded Jun. 19, 2014).
Fialho, S. L. et al., "New vehicle based on a microemulsion for topical ocular administration of dexamethasone", *Clinical & Experimental Ophthalmology*, 32(6):626-632 (Belo Horizonte, Brazil, Dec. 1, 2004).
Radomska-Soukharev, A. et al., "Microemulsions as potential ocular drug delivery systems: phase diagrams and physical properties depending on ingredients", *Acta Poloniae Pharmaceutica—Drug Research*, 62(6):465-471 (Polish Pharmaceutical Society, Warsaw, Poland Nov. 1, 2005).

Vandamme, Th. F., "Microemulsions as ocular drug delivery systems: recent developments and future challenges", *Progress in Retinal and Eye Research*, 21(1):15-34 (Oxford, United Kingdom, Jan. 1, 2002).

International Search Report and Written Opinion from corresponding PCT application PCT/US2014/025773 dated Jul. 4, 2014.

* cited by examiner

*Primary Examiner* — Aradhana Sasan

(74) *Attorney, Agent, or Firm* — Alan W. Steele; Foley Hoag LLP

(57) ABSTRACT

Provided are pharmaceutical carriers based on oil-in-water microemulsions and methods of making same. Also provided are pharmaceutical compositions comprising a carrier of the invention and a lipophilic active pharmaceutical ingredient (API), as well as methods for making same. The pharmaceutical compositions are particularly suitable for use in formulating lipophilic APIs for topical administration to the eye. Specifically included are pharmaceutical compositions comprising fenofibrate or fenofibric acid as API. Also provided is a method of treating a disease of the posterior segment of the eye. Also provided is a pharmaceutical composition comprising a compound represented by

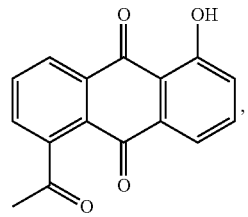

formulated for topical administration to the eye.

20 Claims, 6 Drawing Sheets

|   | 1 | 2 | 3 | 4 | 5 | 6 | 7 | 8 | 9 | 10 |
|---|---|---|---|---|---|---|---|---|---|----|
| A | 500 µl / 500 µl | 475 µl / 525 µl | 450 µl / 550 µl | 425 µl / 575 µl | 400 µl / 600 µl | 375 µl / 625 µl | 350 µl / 650 µl | 325 µl / 675 µl | 300 µl / 700 µl | 275 µl / 725 µl |
| B | 250 µl / 750 µl | 225 µl / 775 µl | 200 µl / 800 µl | 175 µl / 825 µl | 150 µl / 850 µl | 125 µl / 875 µl | 100 µl / 900 µl | 75 µl / 925 µl | 50 µl / 950 µl | 25 µl / 975 µl |

MICROEMULSION TOPICAL DELIVERY PLATFORM

RELATED APPLICATION

This application claims benefit of U.S. Provisional Patent Application No. 61/784,005, filed Mar. 14, 2013.

BACKGROUND OF THE INVENTION

Delivery of active pharmaceutical ingredients (APIs) to the eye may be achieved most conveniently by topical administration to the eye. However, topical delivery of APIs to the eye is commonly limited by a number of factors, including low residence time, poor penetration and delivery to target tissue, and physiological barriers to delivery. These limiting factors are particularly significant for diseases affecting the posterior segment of the eye, and for this reason it is common to resort to other routes of administration, e.g., intraocular (intravitreal) injection and systemic administration, to deliver APIs to the posterior segment of the eye.

Of course, intravitreal injection is invasive and requires highly specialized conditions including performance by an ophthalmologist in an operating room. Moreover, intravitreal injection carries attendant risks of infection and, in the case of intravitreal inserts, displacement.

On the other hand, systemic administration, e.g., intravenous injection, while less demanding technically, is subject to physiologic barriers to success. For example, the blood-retina barrier (BRB), like the blood-brain barrier (BBB), limits APIs from reaching the interior of the eye. Moreover, systemic administration may require unacceptably high dosages of API in order to achieve efficacious drug levels within the eye.

Microemulsions are thermodynamically stable and isotropic formulations composed of a polar phase (e.g., water), a non-polar phase (e.g., oil), surfactant, and co-surfactant. Unlike nanoemulsions, microemulsions form without the need for input energy; they form essentially spontaneously. Certain microemulsions, characterized by their clarity, stability, and the possibility of sterilization, represent candidate topical delivery platforms for APIs directed to the eye.

The eye is divided into two anatomical compartments, called the anterior chamber and the posterior chamber. The smaller anterior chamber includes all structures including and anterior to the lens, e.g., the cornea, aqueous humor, iris, and the lens. The much larger posterior segment includes all remaining structures, i.e., all structures posterior to the lens. These structures include, inter alia, the vitreous humor, retina, retinal blood vessels, macula, choroid, part of the sclera, and optic nerve.

SUMMARY OF THE INVENTION

The invention concerns specific formulations of, and methods of making, microemulsions and microemulsion formulations which useful as pharmaceutical carriers. In a broad sense, the microemulsions and microemulsion formulations may be used for topical delivery of active pharmaceutical ingredients, particularly lipophilic APIs, to any tissue. It has been found, for example, that microemulsions and microemulsion formulations of the invention are suitable for delivering therapeutically meaningful amounts of certain APIs to internal structures of the eye. The microemulsions and microemulsion formulations of the invention are suitable for topical administration to the eye, for example in the form of eyedrops. Surprisingly, topical delivery of microemulsion formulations according to the invention is effective to treat even diseases of the posterior segment of the eye.

An aspect of the invention is a pharmaceutical carrier suitable for topical administration to the eye, comprising:
 an oil-in-water microemulsion comprising
  (i) an oil selected from the group consisting of isopropyl myristate, isopropyl palmitate, and medium chain triglycerides;
  (ii) a pair of surfactants selected from the group consisting of two polysorbates, a polysorbate and propylene glycol, a polysorbate and glycerol, a polysorbate and triacetin (1,2,3-triacetoxypropane), cremophor EL (polyethoxylated castor oil) and triacetin (1,2,3-triacetoxypropane), and cremophor EL (polyethoxylated castor oil) and propylene glycol; and
  (iii) water,
 wherein:
  the water represents 50 to about 95 percent (w/w) of the pharmaceutical carrier;
  the oil and surfactants represent substantially all of the remainder of the pharmaceutical carrier; and
  the ratio of percent (w/w) total surfactant to percent (w/w) oil is at least about 10:1.

An aspect of the invention is a method of making the pharmaceutical carrier of the invention. The method comprises the steps of combining the oil and the pair of surfactants, to yield an oil/surfactant mixture; and combining the oil/surfactant mixture with the water.

An aspect of the invention is a pharmaceutical composition, comprising a lipophilic active pharmaceutical ingredient (API) and the pharmaceutical carrier of the invention, wherein the pharmaceutical composition is formulated for topical administration to the eye.

An aspect of the invention is a method of making the pharmaceutical composition of the invention. The method comprises the steps of combining the oil, the pair of surfactants, and the lipophilic active pharmaceutical ingredient (API), to yield an oil/surfactant/API mixture; and combining the oil/surfactant/API mixture with the water.

An aspect of the invention is method of treating a disease of the posterior segment of the eye. The method comprises the step of topically administering to an eye of a subject in need thereof a composition comprising:
 an oil-in-water microemulsion comprising
  (i) an oil selected from the group consisting of isopropyl myristate, isopropyl palmitate, and medium chain triglycerides;
  (ii) a pair of surfactants selected from the group consisting of two polysorbates, a polysorbate and propylene glycol, a polysorbate and glycerol, a polysorbate and triacetin (1,2,3-triacetoxypropane), cremophor EL (polyethoxylated castor oil) and triacetin (1,2,3-triacetoxypropane), and cremophor EL (polyethoxylated castor oil) and propylene glycol;
  (iii) water; and
  (iv) a therapeutically effective amount, for treating a disease of the posterior segment of the eye, of a lipophilic active pharmaceutical ingredient (API),
 wherein:
  the API represents about 0.01 to about 5 percent (w/v) of the composition;
  the water represents 50 to about 95 percent (w/w) of the composition;
  the oil and surfactants represent substantially all of the remainder of the composition;
  the ratio of percent (w/w) total surfactant to percent (w/w) oil is at least about 10:1; and
  the composition is formulated for topical administration to the eye.

In one embodiment, the API is represented by

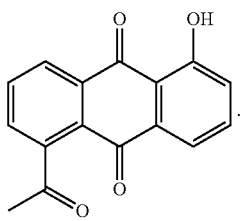 [SMILES: CC(=O)c1cccc2c1C(=O)c1cccc(O)c1C2=O]

In one embodiment, the disease of the posterior segment of the eye is characterized by inflammation, neovascularization, vascular leakage, fibrosis, or any combination thereof.

In one embodiment, the disease of the posterior segment of the eye is selected from the group consisting of: age-related macular degeneration, diabetic retinopathy, posterior uveitis, retinal edema, macular edema, and retinal vein occlusion.

In one embodiment, the disease of the posterior segment of the eye is age-related macular degeneration.

In one embodiment, the disease of the posterior segment of the eye is diabetic retinopathy.

An aspect of the invention is pharmaceutical composition, comprising an effective amount, for treating a disease of the posterior segment of the eye, of a compound represented by

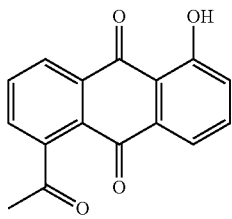

and the pharmaceutical carrier of the invention, wherein the pharmaceutical composition is formulated for topical administration to the eye.

In one embodiment, the pharmaceutical composition is formulated as eyedrops.

DETAILED DESCRIPTION

Figure 1:
FIG. 1 is a pair of photographic images of a single series of twenty clear glass vials containing various formulations of water, oil, and surfactant; and a map representing the formulations in the vials. The vial at the left of the upper photo corresponds to map position A1, and successive vials to the right correspond to map positions A2, A3, etc. The vial at the left of the lower photo corresponds to map position B1, and successive vials to the right correspond to map positions B2, B3, etc. Vial A1 contains (i) 500 μL of oil phase comprised of 90 percent 3:1 Cremophor EL:propylene glycol surfactant/co-surfactant mixture/10 percent isopropyl myristate, and (ii) 500 μL water. Vial A2 comprises (i) 475 μL of the same oil phase, and (ii) 525 μL water. This successive dilution continues until reaching vial B10, which comprises (i) 25 μL of the same oil phase, and (ii) 975 μL water. Clear formulations represent microemulsions.
Figure 1:

As described herein, Applicant has identified, through exhaustive trial-and-error analysis of many combinations of possible components, a group of microemulsion formulations particularly well suited for use in topical administration of lipophilic drugs, including, in particular, for ophthalmic use. The microemulsion formulations are clear, stable, well tolerated, and capable of delivering therapeutically effective amounts of active pharmaceutical ingredients to target sites, including sites within the eye. Surprisingly, the microemulsion formulations of the invention are capable of delivering therapeutically effective amounts of active pharmaceutical ingredients to the posterior segment of the eye following topical administration to the eye.

An aspect of the invention is a pharmaceutical carrier suitable for topical administration to the eye, comprising:

an oil-in-water microemulsion comprising (i) an oil selected from the group consisting of isopropyl myristate, isopropyl palmitate, medium chain triglycerides, and any combination thereof;

(ii) a pair of surfactants selected from the group consisting of two polysorbates, a polysorbate and propylene glycol, a polysorbate and glycerol, a polysorbate and triacetin (1,2,3-triacetoxypropane), cremophor EL (polyethoxylated castor oil) and triacetin (1,2,3-triacetoxypropane), and cremophor EL (polyethoxylated castor oil) and propylene glycol; and (iii) water, wherein:

the water represents 50 to about 95 percent (w/w) of the pharmaceutical carrier;

the oil and surfactants represent substantially all of the remainder of the pharmaceutical carrier; and the ratio of percent (w/w) total surfactant to percent (w/w) oil is at least about 10:1.

As used herein, an "oil-in-water microemulsion" is a microemulsion comprised of at least 50 percent (w/w) water, at least one organic chemical that is normally at least substantially immiscible in water (i.e., an oil), and at least two surfactants (sometimes referred to as surfactant and co-surfactant). The dispersed oil phase is dispersed as droplets in the continuous (water) phase, where the droplets typically have a mean diameter of less than about 300 nm, e.g., about 5 nm to about 200 nm. A microemulsion characteristically has a clear or translucent appearance on visual inspection because the droplets are too small to scatter light of visible wavelengths. Microemulsions typically have viscosities lower than liquid crystals, e.g., about 10-400 mPa·s.

As used herein, "medium chain triglyceride" or "MCT" refers to triglyceride for which at least 90 percent of fatty acids are made of 8-10 carbon atoms. Examples include Myglyol® 810 or 812 (triesters of glycerol, capric acid, and caprylic acid; Sasol Germany GmbH, Witten, Germany) and oils obtained by hydrolysis, fractionation, and esterification of coconut oil. Bach, A et al. (1982) *Am J Clin Nutr* 36:293. MCTs are more water-soluble than long-chain triglycerides, yet they accommodate large amounts of lipophilic drugs.

As used herein, the term "surfactant" takes its usual meaning, and a "pair of surfactants" refers to two surfactants or, equivalently, a surfactant and a co-surfactant. The two surfactants can be present in the same or different amounts.

As used herein, the term "polysorbate" refers generally to a polyoxyethylene derivative of sorbitan fatty acid ester. Common commercial preparations of polysorbates are sold under the name Tween®, Alkest, or Canarcel. In the nomenclature of polysorbates, the numeric designation following polysorbate (or Tween®) refers to the lipophilic group. For example, polysorbate 20 is a monolaurate ester, and polysorbate 80 is a monooleate ester.

Cremophor® EL (BASF SE), is a version of polyethoxylated castor oil, the major component of which is glycerol polyethylene glycol ricinoleate. Additional components include free polyethylene glycols and ethoxylated glycerol. It is prepared by reacting 35 moles of ethylene oxide with each mole of castor oil. The product has been given CAS number 61791-12-6.

In one embodiment, the water represents 50 percent (w/w) of the pharmaceutical carrier.

In one embodiment, the water represents at least about 55 percent (w/w) of the pharmaceutical carrier.

In one embodiment, the water represents at least about 60 percent (w/w) of the pharmaceutical carrier.

In one embodiment, the water represents at least about 65 percent (w/w) of the pharmaceutical carrier.

In one embodiment, the water represents at least about 70 percent (w/w) of the pharmaceutical carrier.

In one embodiment, the water represents at least about 75 percent (w/w) of the pharmaceutical carrier.

In one embodiment, the water represents at least about 80 percent (w/w) of the pharmaceutical carrier. In one embodiment, the water represents at least about 85 percent (w/w) of the pharmaceutical carrier.

In one embodiment, the water represents at least about 90 percent (w/w) of the pharmaceutical carrier.

The term "w/w" as used herein means ratio of weight of component (in grams) to weight of solution (in grams), where weight of solution refers to the total weight of the oil, water, and surfactant. As an example, 1 percent (w/w) isopropyl myristate denotes 1 g isopropyl myristate per 100 g total weight.

The term "w/v" as used herein means ratio of weight (in grams) to volume (in mL), where volume refers to the final volume. As an example, 1 percent (w/v) isopropyl myristate denotes 1 g isopropyl myristate per 100 mL final volume.

As used herein in connection with any particular numerical value, in one embodiment the term "about" means that particular numerical value plus or minus 5% of that particular value. Thus, for example, the term "about 1 percent (w/w)" can be understood to embrace a range of values from 0.95 to 1.05 percent (w/w). Similarly, the term "about 10:1" can be understood to embrace a range of values from 9.5:1 to 10.5:1.

Moreover, the term "at least about 10:1" in one embodiment means from about 10:1 to about 20:1. In additional separate embodiments, the term "at least about 10:1" means from about 10:1 to about 11:1; from about 10:1 to about 12:1; from about 10:1 to about 13:1; from about 10:1 to about 14:1; and from about 10:1 to about 15:1.

In one embodiment, the term "at least about 10:1" means about 10:1.

In one embodiment, the oil is isopropyl myristate.

In one embodiment, the oil is isopropyl palmitate.

In one embodiment, the oil is medium chain triglycerides.

In one embodiment, the pair of surfactants is two polysorbates. For example, in one embodiment, the pair of surfactants is polysorbate 20 and polysorbate 80.

In one embodiment, the pair of surfactants is a polysorbate and propylene glycol.

In one embodiment, the pair of surfactants is a polysorbate and glycerol.

In one embodiment, the pair of surfactants is a polysorbate and triacetin (1,2,3-triacetoxypropane).

In one embodiment, the pair of surfactants is cremophor EL (polyethoxylated castor oil) and triacetin (1,2,3-triacetoxypropane).

In one embodiment, the pair of surfactants is cremophor EL (polyethoxylated castor oil) and propylene glycol.

An aspect of the invention is a method of making the pharmaceutical carrier just described above, i.e., a method of making the pharmaceutical carrier of the invention. The method includes the steps of combining the oil and the pair of surfactants, to yield an oil/surfactant mixture; and combining the oil/surfactant mixture with the water. The combined components will form a microemulsion essentially spontaneously. That is, thorough mixing alone, for example by rocking or gentle vortexing, sufficient to bring all components into contact, should suffice to form the microemulsion.

Preferred microemulsions are optically clear and homogeneous to visual inspection, and thermodynamically stable.

The method of making the pharmaceutical carrier optionally can include the further step of sterilizing the formed pharmaceutical carrier, for example by sterile filtering or autoclaving for 20 min at 121° C.

The method of making the pharmaceutical carrier optionally can include the further step of sizing the droplets.

An aspect of the invention is a pharmaceutical composition, comprising a lipophilic active pharmaceutical ingredient (API) and the pharmaceutical carrier of the invention, wherein the pharmaceutical composition is formulated for topical administration to the eye.

The API can be any lipophilic API. As used herein, the term "lipophilic" means substantially more soluble in lipid, oil, or fat than in water at room temperature. In one embodiment, the term "lipophilic" further means having a solubility in water at room temperature of less than or equal to 30 mg/mL. In one embodiment, the term "lipophilic" further means having a solubility in water at room temperature of less than or equal to 10 mg/mL. In one embodiment, the term "lipophilic" further means having a solubility in water at room temperature of less than or equal to 1 mg/mL. In one embodiment, the term "lipophilic" further means having a solubility in water at room temperature of less than or equal to 0.5 mg/mL. In one embodiment, the term "lipophilic" further means having a solubility in water at room temperature of less than or equal to 0.2 mg/mL. In one embodiment, the term "lipophilic" further means having a solubility in water at room temperature of less than or equal to 0.1 mg/mL. In one embodiment, the term "lipophilic" further means negligibly soluble in water at room temperature.

In one embodiment, the lipophilic API is selected from the group consisting of anti-inflammatory agents, anti-infective agents, anti-allergic agents, antihistamines, antiproliferative agents, anti-angiogenic agents, anti-oxidants, antihypertensive agents, neuroprotective agents, cell receptor agonists, cell receptor antagonists, immunomodulating agents, immunosuppressive agents, intraocular pressure lowering agents, α2-adrenergic receptor agonists, β1-adrenergic receptor antagonists, carbonic anhydrase inhibitors, cholinesterase inhibitor miotics, prostaglandins, prostaglandin receptor agonists, mast cell degranulation inhibitors (mast cell stabilizers), thromboxane A2 mimetics, protein kinase inhibitors, prostaglandin F derivatives, prostaglandin $F_{2\alpha}$ receptor antagonists, cyclooxygenase-2 inhibitors, muscarinic agents, and any combination thereof In one embodiment, the lipophilic API is selected from the group consisting of adaprolol maleate, cyclosporine A, fenofibrate, fenofibric acid, indomethacin, miconazole, pilocarpine, piroxicam, and $\Delta^8$-THC.

In one embodiment, the lipophilic API is fenofibrate

In one embodiment, the lipophilic API is fenofibric acid.

In one embodiment, the lipophilic API is an API that is useful for the treatment of a disease of anterior segment of the eye.

A "disease of the anterior segment of the eye" refers to any disease of the anterior segment of the eye. Examples of diseases of the anterior segment of the eye include, without limitation, cataract, corneal neovascularization, dry eye (keratoconjunctivitis sicca), Fuchs' dystrophy, glaucoma, keratitis (including herpes keratitis), and keratoconus. In one embodiment, a disease of the anterior segment of the eye specifically excludes diseases of the lens, e.g., cataract. In one embodiment, a disease of the anterior segment of the eye is glaucoma.

In one embodiment, the API is an API that is useful for the treatment of a disease of the posterior segment of the eye.

As used herein, the term "posterior segment of the eye" takes its usual meaning and refers to that part of the eye bounded anteriorly by the lens and anterior hyaloid membrane, and extending to the back of the eye. It is much larger than the anterior segment and includes the vitreous humor, retina, retinal blood vessels, macula, choroid, and optic nerve.

A "disease of the posterior segment of the eye" refers to any disease of the posterior segment of the eye. Of particular interest are inflammatory, autoimmune, vascular, and certain infectious diseases of the posterior segment of the eye. Diseases of the posterior segment of the eye specifically include, without limitation, age-related macular degeneration (AMD), diabetic retinopathy, posterior uveitis, retinal edema, macular edema, and retinal vein occlusion. AMD specifically includes both dry AMD and wet AMD. Each of these diseases or conditions is well known in the art and need not be further described here.

In one embodiment, the disease of the posterior segment of the eye is characterized by inflammation, neovascularization, vascular leakage, fibrosis, or any combination thereof.

In one embodiment, the disease of the posterior segment of the eye is selected from the group consisting of: age-related macular degeneration, diabetic retinopathy, posterior uveitis, retinal edema, macular edema, and retinal vein occlusion.

As used herein, "topical administration" refers to localized administering to a surface of a tissue. Topical administration to the eye refers to localized administering to a surface of an eye, for example, to any exterior aspect of the eye normally accessible between the eyelids. Topical administration to the eye generally may be achieved, for example, with drops, irrigants, ointments, or sprays.

In one embodiment, the pharmaceutical composition of the invention is formulated as eyedrops. For example, the composition may be presented in a rigid bottle fitted with a combination screw-cap/bulb pipette dropper cap. In one embodiment the composition is presented in a squeeze bottle fitted with a tip constructed and arranged to serve as a dropper and a removable cap to cover the tip. In a typical embodiment the eyedrops are dispensed as 30 microliter to 300 microliter single drops.

An aspect of the invention is method of making the pharmaceutical composition just described. The method includes the steps of combining the oil, the pair of surfactants, and the lipophilic active pharmaceutical ingredient (API), to yield an oil/surfactant/API mixture; and combining the oil/surfactant/API mixture with the water.

The API is included in the pharmaceutical composition in a therapeutically effective amount to treat a particular disease that is to be treated using the pharmaceutical composition.

As used herein, a "therapeutically effective amount" is any amount that is sufficient to achieve a desired therapeutic result. For example, a therapeutically effective amount for treating a disease of the posterior segment of the eye is an amount sufficient to treat a disease of the posterior segment of the eye.

A therapeutically effective amount of a given API for a given disease to be treated can be determined based on existing clinical experience using the API to treat the disease, or through reasonable amounts of experimentation performed in vitro and/or in vivo in animals and/or in human subjects.

The therapeutic amount of the API should be selected so as not to prevent formation of a microemulsion. Generally, the API will be present in an amount less than or equal to about 5 percent (w/v) of the pharmaceutical composition. In various individual embodiments, the amount of API may be selected from 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, and 5.0 percent (w/v).

An aspect of the invention is a method of treating a disease of the posterior segment of the eye. The method includes the step of topically administering to an eye of a subject in need thereof a composition comprising an oil-in-water microemulsion comprising (i) an oil selected from the group consisting of isopropyl myristate, isopropyl palmitate, medium chain triglycerides, and any combination thereof;

(ii) a pair of surfactants selected from the group consisting of two polysorbates, a polysorbate and propylene glycol, a polysorbate and glycerol, a polysorbate and triacetin (1,2,3-triacetoxypropane), cremophor EL (polyethoxylated castor oil) and triacetin (1,2,3-triacetoxypropane), and cremophor EL (polyethoxylated castor oil) and propylene glycol;

(iii) water; and (iv) a therapeutically effective amount, for treating a disease of the posterior segment of the eye, of a lipophilic active pharmaceutical ingredient (API), wherein:

the API represents about 0.01 to about 5 percent (w/v) of the composition;

the water represents 50 to about 95 percent (w/w) of the composition;

the oil and surfactants represent substantially all of the remainder of the composition;

the ratio of percent (w/w) total surfactant to percent (w/w) oil is at least about 10:1; and the composition is formulated for topical administration to the eye.

As used herein, the terms "treat" or "treating" refer to slowing the progression of, halting the progression of, reversing the progression of, or resolving a disease or condition in a subject. In one embodiment, "treat" or "treating" further refer to preventing a disease or condition in a subject.

As used herein, a "subject" refers to a mammal. In one embodiment, a subject is a human.

The subject can administer the composition to itself, or a caregiver can administer the composition to the eye of the subject.

In one embodiment, the administering is administering once a day. In one embodiment, the administering is administering more than once a day. In various embodiments, the administering is administering 2 times, 3 times, 4 times, 5 times, 6 times, 7 times, 8 times, 9 times, 10 times, 11 times, or 12 times a day. In one embodiment, the administering is administering one time to six times a day.

In one embodiment, the administering involves topically administering a single drop of the composition to the eye to be treated. Such single-drop administration can include administration 1 time, 2 times, 3 times, 4 times, 5 times, 6 times, 7 times, 8 times, 9 times, 10 times, 11 times, or 12 times a day.

In one embodiment, the lipophilic API is selected from the group consisting of adaprolol maleate, cyclosporine A, fenofibrate, fenofibric acid, indomethacin, miconazole, pilocarpine, piroxicam, and $\Delta^8$-THC.

In one embodiment, the lipophilic API is fenofibrate

In one embodiment, the lipophilic API is fenofibric acid.

In one embodiment, the lipophilic API is 1-acetyl-5-hydroxyanthracene-9,10-dione, represented by

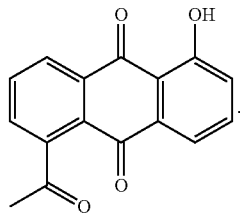 [SMILES: CC(=O)c1cccc2c1C(=O)c1cccc(O)c1C2=O]

This compound, also known as CLT-005, is disclosed in U.S. Pat. No. 8,058,316 to Farjo, the entire content of which is incorporated herein by reference.

In one embodiment, the disease of the posterior segment of the eye is characterized by inflammation, neovascularization, vascular leakage, fibrosis, or any combination thereof In one embodiment, the disease of the posterior segment of the eye is selected from the group consisting of: age-related macular degeneration, diabetic retinopathy, posterior uveitis, retinal edema, macular edema, and retinal vein occlusion.

In one embodiment, the disease of the posterior segment of the eye is age-related macular degeneration.

In one embodiment, the disease of the posterior segment of the eye is dry age-related macular degeneration.

In one embodiment, the disease of the posterior segment of the eye is wet age-related macular degeneration.

In one embodiment, the disease of the posterior segment of the eye is diabetic retinopathy.

An aspect of the invention is a pharmaceutical composition, comprising an effective amount, for treating a disease of the posterior segment of the eye, of a compound represented by

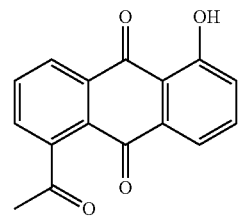 [SMILES: CC(=O)c1cccc2c1C(=O)c1cccc(O)c1C2=O]

and the pharmaceutical carrier the invention, wherein the pharmaceutical composition is formulated for topical administration to the eye.

In one embodiment, the pharmaceutical composition is formulated as eyedrops.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Microemulsion Formulation Library

In order to identify candidate microemulsions useful in accordance with the invention, over twenty thousand (20,000) formulations representing different combinations of different oils and surfactants were prepared and characterized. Of the tens of thousands of formulations examined, nearly a thousand were identified as candidate microemulsions. A pseudoternary phase diagram was prepared or could be prepared based on data obtained for each particular combination of oil and surfactants.

As described in Examples 2-4 below, oil-in-water microemulsion formulations comprised of (i) oils selected from isopropyl myristate, isopropyl palmitate, and medium chain triglyceride, and (ii) pairs of surfactants selected from Tween® 20, Tween® 80, polypropylene glycol, glycerol, triacetin, and Cremophor® EL were identified.

In addition, each microemulsion was characterized for stability.

In an ongoing effort to characterize the microemulsions, certain of the microemulsions have been tested for ocular tolerability in mice.

In an ongoing effort to characterize the microemulsions, certain of the microemulsions have been used in combination with up to 5 percent (w/v) CLT-005.

FIG. 1 presents representative results from part of one single combination of oil, surfactants, and water.

Figure 2:
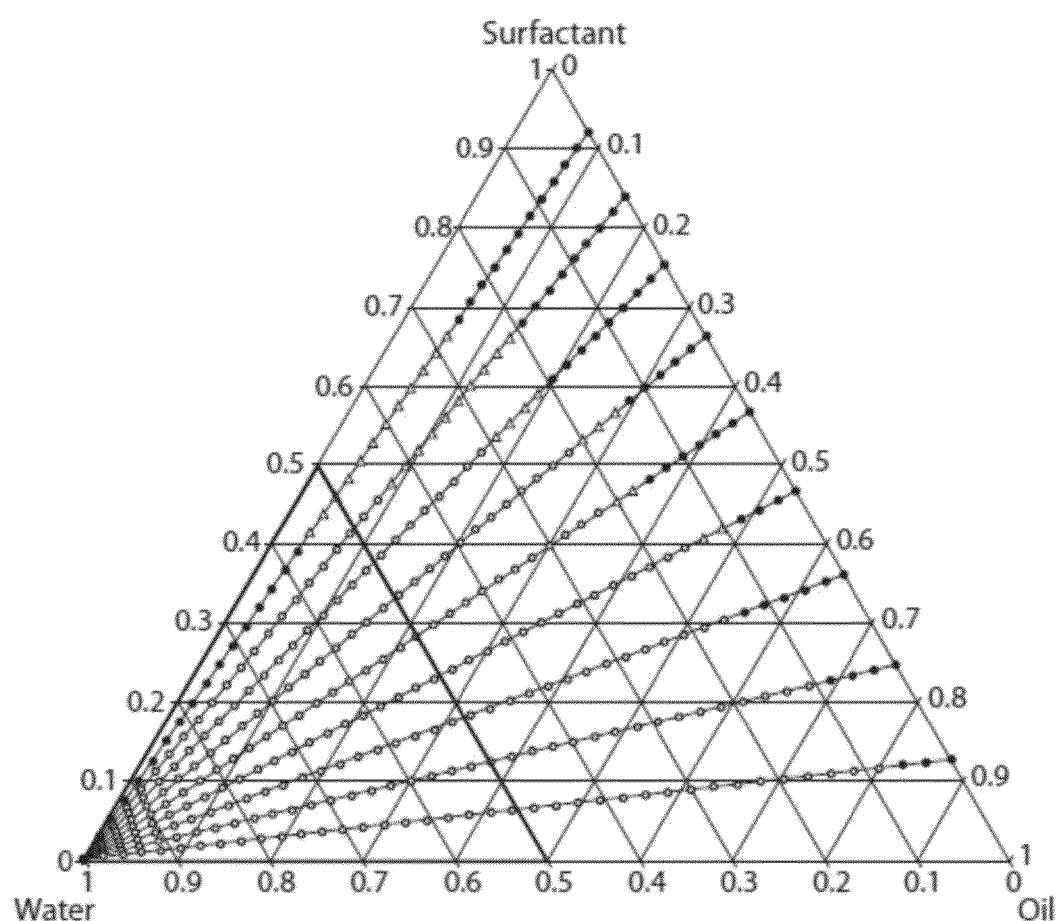
FIG. 2 is a representative pseudoternary phase diagram with 100 percent water, 100 percent oil, and 100 percent total surfactant at the apices labeled Water, Oil, and Surfactant, respectively. The area enclosed by heavier lines represents potential oil-in-water microemulsion space (water>50 percent). Each symbol represents a data point for actual combinations of different water/oil/total surfactant combinations tested in the Examples. (Microemulsions correspond to only a subset of these points.)

FIG. 2 presents a representative pseudoternary phase diagram generated in accordance with this systematic study. Each filled circle on the plot represents a microemulsion. Each unfilled triangle on the plot represents a clear mixture that is not a microemulsion, e.g., a liquid crystal. Each unfilled circle on the plot represents a cloudy mixture.

Example 2

Microemulsion Formulations Comprised of Isopropyl Myristate

Tables 1-26 present representative formulations of microemulsions comprised of isopropyl myristate and pairs of surfactants selected from Tween® 20 ("T20"), Tween® 80 ("T80"), polypropylene glycol ("P"), glycerol ("G"), triacetin ("TriAc"), and Cremophor® EL ("CEL"). Numerical values are given as percent (w/w). "Surfactant" represents the percent (w/w) of total surfactant in each formulation.

TABLE 1

Isopropyl Myristate

| T20:T80 | ID | Water | Oil | Surfactant |
|---|---|---|---|---|
| 1 to 1 | MEM0078 | 0.473 | 0.040 | 0.487 |
| | MEM0042 | 0.498 | 0.038 | 0.464 |
| | MEM0043 | 0.523 | 0.036 | 0.440 |
| | MEM0044 | 0.548 | 0.035 | 0.417 |
| | MEM0045 | 0.574 | 0.033 | 0.394 |
| | MEM0046 | 0.599 | 0.031 | 0.370 |
| | MEM0047 | 0.625 | 0.029 | 0.346 |
| | MEM0048 | 0.651 | 0.027 | 0.322 |
| | MEM0079 | 0.972 | 0.002 | 0.026 |

TABLE 2

Isopropyl Myristate

| T20:T80 | ID | Water | Oil | Surfactant |
|---|---|---|---|---|
| 2 to 1 | MEM0080 | 0.484 | 0.041 | 0.475 |
| | MEM0056 | 0.509 | 0.039 | 0.452 |
| | MEM0057 | 0.534 | 0.037 | 0.429 |
| | MEM0058 | 0.559 | 0.035 | 0.406 |
| | MEM0059 | 0.584 | 0.033 | 0.383 |

TABLE 3

Isopropyl Myristate

| T20:T80 | ID | Water | Oil | Surfactant |
|---|---|---|---|---|
| 3 to 1 | MEM0081 | 0.477 | 0.041 | 0.482 |
| | MEM0060 | 0.502 | 0.039 | 0.459 |
| | MEM0061 | 0.527 | 0.037 | 0.436 |

TABLE 4

Isopropyl Myristate

| T20:T80 | ID | Water | Oil | Surfactant |
|---|---|---|---|---|
| 4 to 1 | MEM0082 | 0.475 | 0.040 | 0.485 |
| | MEM0062 | 0.500 | 0.039 | 0.461 |
| | MEM0063 | 0.525 | 0.037 | 0.438 |

TABLE 5

Isopropyl Myristate

| T20:T80 | ID | Water | Oil | Surfactant |
|---|---|---|---|---|
| 5 to 1 | MEM0083 | 0.475 | 0.040 | 0.484 |
| | MEM0064 | 0.500 | 0.039 | 0.461 |

TABLE 6

Isopropyl Myristate

| T20:T80 | ID | Water | Oil | Surfactant |
|---|---|---|---|---|
| 1 to 2 | MEM0084 | 0.485 | 0.041 | 0.473 |
| | MEM0085 | 0.510 | 0.039 | 0.450 |
| | MEM0086 | 0.535 | 0.037 | 0.427 |
| | MEM0087 | 0.561 | 0.035 | 0.404 |
| | MEM0088 | 0.586 | 0.033 | 0.381 |
| | MEM0089 | 0.611 | 0.031 | 0.358 |
| | MEM0090 | 0.636 | 0.029 | 0.334 |
| | MEM0091 | 0.662 | 0.027 | 0.311 |
| | MEM0092 | 0.688 | 0.025 | 0.287 |
| | MEM0093 | 0.713 | 0.023 | 0.264 |
| | MEM0094 | 0.739 | 0.021 | 0.240 |
| | MEM0095 | 0.974 | 0.002 | 0.024 |

MEM0084-MEM0089 were unstable.

TABLE 7

Isopropyl Myristate

| T20:T80 | ID | Water | Oil | Surfactant |
|---|---|---|---|---|
| 1 to 3 | MEM0096 | 0.477 | 0.041 | 0.482 |
| | MEM0097 | 0.502 | 0.039 | 0.459 |
| | MEM0098 | 0.527 | 0.037 | 0.436 |
| | MEM0099 | 0.552 | 0.035 | 0.413 |
| | MEM0049 | 0.578 | 0.033 | 0.390 |
| | MEM0027 | 0.603 | 0.031 | 0.366 |
| | MEM0028 | 0.629 | 0.029 | 0.342 |
| | MEM0050 | 0.654 | 0.027 | 0.319 |
| | MEM0100 | 0.680 | 0.025 | 0.295 |
| | MEM0101 | 0.706 | 0.023 | 0.271 |
| | MEM0051 | 0.732 | 0.021 | 0.247 |
| | MEM0102 | 0.758 | 0.019 | 0.223 |
| | MEM0103 | 0.785 | 0.017 | 0.198 |
| | MEM0104 | 0.811 | 0.015 | 0.174 |
| | MEM0105 | 0.838 | 0.013 | 0.150 |
| | MEM0106 | 0.865 | 0.010 | 0.125 |
| | MEM0107 | 0.891 | 0.008 | 0.100 |
| | MEM0108 | 0.918 | 0.006 | 0.075 |
| | MEM0109 | 0.945 | 0.004 | 0.050 |
| | MEM0110 | 0.973 | 0.002 | 0.025 |

MEM0096-MEM0099 were unstable.

TABLE 8

Isopropyl Myristate

| T20:T80 | ID | Water | Oil | Surfactant |
|---|---|---|---|---|
| 1 to 4 | MEM0111 | 0.478 | 0.041 | 0.482 |
| | MEM0112 | 0.503 | 0.039 | 0.459 |
| | MEM0113 | 0.528 | 0.037 | 0.435 |
| | MEM0114 | 0.553 | 0.035 | 0.412 |
| | MEM0115 | 0.578 | 0.033 | 0.389 |
| | MEM0116 | 0.611 | 0.031 | 0.358 |
| | MEM0117 | 0.636 | 0.029 | 0.334 |
| | MEM0052 | 0.662 | 0.027 | 0.311 |
| | MEM0053 | 0.687 | 0.025 | 0.287 |
| | MEM0054 | 0.713 | 0.023 | 0.264 |
| | MEM0055 | 0.739 | 0.021 | 0.240 |
| | MEM0118 | 0.765 | 0.019 | 0.217 |
| | MEM0119 | 0.785 | 0.017 | 0.198 |
| | MEM0120 | 0.812 | 0.015 | 0.174 |
| | MEM0121 | 0.838 | 0.013 | 0.149 |
| | MEM0122 | 0.865 | 0.011 | 0.125 |
| | MEM0123 | 0.892 | 0.008 | 0.100 |
| | MEM0124 | 0.919 | 0.006 | 0.075 |
| | MEM0125 | 0.946 | 0.004 | 0.050 |
| | MEM0126 | 0.973 | 0.002 | 0.025 |

MEM0111-MEM0115 were unstable.

TABLE 9

Isopropyl Myristate

| T20:T80 | ID | Water | Oil | Surfactant |
|---|---|---|---|---|
| 1 to 5 | MEM0127 | 0.485 | 0.041 | 0.473 |
| | MEM0128 | 0.510 | 0.039 | 0.450 |
| | MEM0129 | 0.535 | 0.037 | 0.427 |
| | MEM0130 | 0.561 | 0.035 | 0.404 |
| | MEM0131 | 0.586 | 0.033 | 0.381 |
| | MEM0132 | 0.611 | 0.031 | 0.358 |
| | MEM0133 | 0.636 | 0.029 | 0.334 |
| | MEM0134 | 0.662 | 0.027 | 0.311 |
| | MEM0135 | 0.688 | 0.025 | 0.287 |
| | MEM0136 | 0.713 | 0.023 | 0.264 |
| | MEM0137 | 0.739 | 0.021 | 0.240 |
| | MEM0138 | 0.765 | 0.019 | 0.217 |
| | MEM0139 | 0.790 | 0.017 | 0.193 |
| | MEM0140 | 0.816 | 0.015 | 0.169 |
| | MEM0141 | 0.842 | 0.013 | 0.145 |
| | MEM0142 | 0.868 | 0.011 | 0.121 |
| | MEM0143 | 0.895 | 0.008 | 0.097 |
| | MEM0144 | 0.921 | 0.006 | 0.073 |
| | MEM0145 | 0.947 | 0.004 | 0.049 |
| | MEM0146 | 0.974 | 0.002 | 0.024 |

MEM0127-MEM0131 were unstable.

TABLE 10

Isopropyl Myristate

| T80:P | ID | Water | Oil | Surfactant |
|---|---|---|---|---|
| 2 to 1 | MEM0375 | 0.492 | 0.042 | 0.466 |
| | MEM0376 | 0.517 | 0.040 | 0.443 |
| | MEM0377 | 0.542 | 0.038 | 0.420 |
| | MEM0378 | 0.567 | 0.036 | 0.397 |
| | MEM0379 | 0.592 | 0.034 | 0.374 |
| | MEM0380 | 0.618 | 0.032 | 0.351 |

TABLE 11

Isopropyl Myristate

| T80:P | ID | Water | Oil | Surfactant |
|---|---|---|---|---|
| 3 to 1 | MEM0381 | 0.492 | 0.042 | 0.466 |
| | MEM0382 | 0.517 | 0.040 | 0.443 |
| | MEM0383 | 0.542 | 0.038 | 0.420 |
| | MEM0384 | 0.567 | 0.036 | 0.397 |
| | MEM0385 | 0.592 | 0.034 | 0.374 |
| | MEM0386 | 0.617 | 0.031 | 0.351 |
| | MEM0387 | 0.642 | 0.029 | 0.328 |
| | MEM0388 | 0.668 | 0.027 | 0.305 |
| | MEM0389 | 0.693 | 0.025 | 0.282 |
| | MEM0390 | 0.744 | 0.021 | 0.235 |
| | MEM0391 | 0.769 | 0.019 | 0.212 |
| | MEM0392 | 0.795 | 0.017 | 0.188 |
| | MEM0393 | 0.820 | 0.015 | 0.165 |
| | MEM0394 | 0.846 | 0.013 | 0.142 |
| | MEM0395 | 0.871 | 0.011 | 0.118 |
| | MEM0396 | 0.897 | 0.008 | 0.095 |
| | MEM0397 | 0.923 | 0.006 | 0.071 |
| | MEM0398 | 0.948 | 0.004 | 0.047 |
| | MEM0399 | 0.974 | 0.002 | 0.024 |

TABLE 12

Isopropyl Myristate

| T80:P | ID | Water | Oil | Surfactant |
|---|---|---|---|---|
| 4 to 1 | MEM0400 | 0.567 | 0.036 | 0.398 |
| | MEM0401 | 0.592 | 0.034 | 0.375 |
| | MEM0402 | 0.617 | 0.031 | 0.352 |
| | MEM0403 | 0.642 | 0.029 | 0.328 |
| | MEM0404 | 0.667 | 0.027 | 0.305 |

MEM0400 was unstable.

TABLE 13

Isopropyl Myristate

| T80:P | ID | Water | Oil | Surfactant |
|---|---|---|---|---|
| 5 to 1 | MEM0405 | 0.491 | 0.042 | 0.467 |
| | MEM0406 | 0.516 | 0.040 | 0.444 |
| | MEM0407 | 0.541 | 0.038 | 0.421 |
| | MEM0408 | 0.566 | 0.036 | 0.398 |
| | MEM0409 | 0.592 | 0.034 | 0.375 |
| | MEM0410 | 0.617 | 0.031 | 0.352 |
| | MEM0411 | 0.642 | 0.029 | 0.329 |
| | MEM0412 | 0.667 | 0.027 | 0.305 |
| | MEM0413 | 0.693 | 0.025 | 0.282 |
| | MEM0414 | 0.718 | 0.023 | 0.259 |
| | MEM0415 | 0.743 | 0.021 | 0.235 |
| | MEM0416 | 0.769 | 0.019 | 0.212 |
| | MEM0417 | 0.794 | 0.017 | 0.189 |
| | MEM0418 | 0.820 | 0.015 | 0.165 |
| | MEM0419 | 0.846 | 0.013 | 0.142 |
| | MEM0420 | 0.871 | 0.011 | 0.118 |
| | MEM0421 | 0.897 | 0.008 | 0.095 |
| | MEM0422 | 0.923 | 0.006 | 0.071 |
| | MEM0423 | 0.948 | 0.004 | 0.047 |
| | MEM0424 | 0.974 | 0.002 | 0.024 |
| | MEM0425 | 0.949 | 0.008 | 0.042 |
| | MEM0426 | 0.975 | 0.004 | 0.021 |

MEM0405-MEM0408 were unstable.

TABLE 14

Isopropyl Myristate

| T80:G | ID | Water | Oil | Surfactant |
|---|---|---|---|---|
| 1 to 1 | MEM0578 | 0.472 | 0.040 | 0.488 |
|  | MEM0579 | 0.497 | 0.038 | 0.465 |

TABLE 15

Isopropyl Myristate

| T80:G | ID | Water | Oil | Surfactant |
|---|---|---|---|---|
| 3 to 1 | MEM0033 | 0.582 | 0.033 | 0.385 |
|  | MEM0580 | 0.608 | 0.031 | 0.361 |
|  | MEM0581 | 0.633 | 0.029 | 0.338 |
|  | MEM0582 | 0.659 | 0.027 | 0.314 |
|  | MEM0583 | 0.684 | 0.025 | 0.291 |

TABLE 16

Isopropyl Myristate

| T80:G | ID | Water | Oil | Surfactant |
|---|---|---|---|---|
| 4 to 1 | MEM0034 | 0.483 | 0.041 | 0.476 |
|  | MEM0584 | 0.508 | 0.039 | 0.453 |
|  | MEM0585 | 0.533 | 0.037 | 0.429 |
|  | MEM0586 | 0.559 | 0.035 | 0.406 |
|  | MEM0587 | 0.584 | 0.033 | 0.383 |
|  | MEM0588 | 0.609 | 0.031 | 0.360 |
|  | MEM0589 | 0.635 | 0.029 | 0.336 |
|  | MEM0590 | 0.660 | 0.027 | 0.313 |
|  | MEM0591 | 0.686 | 0.025 | 0.289 |
|  | MEM0592 | 0.712 | 0.023 | 0.266 |
|  | MEM0593 | 0.737 | 0.021 | 0.242 |
|  | MEM0594 | 0.763 | 0.019 | 0.218 |
|  | MEM0595 | 0.789 | 0.017 | 0.194 |
|  | MEM0596 | 0.815 | 0.015 | 0.170 |
|  | MEM0597 | 0.841 | 0.013 | 0.146 |
|  | MEM0598 | 0.868 | 0.011 | 0.122 |
|  | MEM0599 | 0.894 | 0.008 | 0.098 |
|  | MEM0600 | 0.920 | 0.006 | 0.073 |
|  | MEM0601 | 0.947 | 0.004 | 0.049 |
|  | MEM0602 | 0.973 | 0.002 | 0.025 |

TABLE 17

Isopropyl Myristate

| T80:G | ID | Water | Oil | Surfactant |
|---|---|---|---|---|
| 5 to 1 | MEM0603 | 0.485 | 0.041 | 0.474 |
|  | MEM0604 | 0.510 | 0.039 | 0.451 |
|  | MEM0605 | 0.535 | 0.037 | 0.428 |
|  | MEM0606 | 0.560 | 0.035 | 0.405 |
|  | MEM0607 | 0.585 | 0.033 | 0.382 |
|  | MEM0608 | 0.610 | 0.031 | 0.358 |
|  | MEM0609 | 0.636 | 0.029 | 0.335 |
|  | MEM0610 | 0.661 | 0.027 | 0.312 |
|  | MEM0611 | 0.687 | 0.025 | 0.288 |
|  | MEM0612 | 0.712 | 0.023 | 0.265 |
|  | MEM0613 | 0.738 | 0.021 | 0.241 |
|  | MEM0614 | 0.764 | 0.019 | 0.217 |
|  | MEM0615 | 0.790 | 0.017 | 0.193 |
|  | MEM0616 | 0.816 | 0.015 | 0.169 |
|  | MEM0617 | 0.842 | 0.013 | 0.145 |
|  | MEM0618 | 0.868 | 0.011 | 0.121 |
|  | MEM0619 | 0.894 | 0.008 | 0.097 |
|  | MEM0620 | 0.921 | 0.006 | 0.073 |
|  | MEM0621 | 0.947 | 0.004 | 0.049 |
|  | MEM0622 | 0.973 | 0.002 | 0.024 |

TABLE 18

Isopropyl Myristate

| T80:TriAc | ID | Water | Oil | Surfactant |
|---|---|---|---|---|
| 1 to 1 | MEM0872 | 0.840 | 0.013 | 0.148 |
|  | MEM0873 | 0.866 | 0.011 | 0.123 |

TABLE 19

Isopropyl Myristate

| T80:TriAc | ID | Water | Oil | Surfactant |
|---|---|---|---|---|
| 2 to 1 | MEM0874 | 0.661 | 0.027 | 0.312 |
|  | MEM0875 | 0.712 | 0.023 | 0.265 |
|  | MEM0876 | 0.738 | 0.021 | 0.242 |
|  | MEM0877 | 0.763 | 0.019 | 0.218 |
|  | MEM0878 | 0.789 | 0.017 | 0.194 |
|  | MEM0879 | 0.815 | 0.015 | 0.170 |
|  | MEM0880 | 0.842 | 0.013 | 0.146 |
|  | MEM0881 | 0.868 | 0.011 | 0.122 |
|  | MEM0882 | 0.894 | 0.008 | 0.098 |
|  | MEM0883 | 0.920 | 0.006 | 0.073 |
|  | MEM0884 | 0.947 | 0.004 | 0.049 |
|  | MEM0885 | 0.973 | 0.002 | 0.025 |

TABLE 20

Isopropyl Myristate

| T80:TriAc | ID | Water | Oil | Surfactant |
|---|---|---|---|---|
| 3 to 1 | MEM0886 | 0.485 | 0.041 | 0.473 |
|  | MEM0023 | 0.510 | 0.039 | 0.450 |
|  | MEM0887 | 0.536 | 0.037 | 0.427 |
|  | MEM0888 | 0.561 | 0.035 | 0.404 |
|  | MEM0889 | 0.586 | 0.033 | 0.381 |
|  | MEM0890 | 0.611 | 0.031 | 0.358 |
|  | MEM0891 | 0.637 | 0.029 | 0.334 |
|  | MEM0892 | 0.662 | 0.027 | 0.311 |
|  | MEM0893 | 0.688 | 0.025 | 0.287 |
|  | MEM0894 | 0.713 | 0.023 | 0.264 |
|  | MEM0895 | 0.739 | 0.021 | 0.240 |
|  | MEM0896 | 0.765 | 0.019 | 0.216 |
|  | MEM0897 | 0.791 | 0.017 | 0.193 |
|  | MEM0898 | 0.816 | 0.015 | 0.169 |
|  | MEM0899 | 0.842 | 0.013 | 0.145 |
|  | MEM0900 | 0.868 | 0.011 | 0.121 |
|  | MEM0901 | 0.895 | 0.008 | 0.097 |
|  | MEM0902 | 0.921 | 0.006 | 0.073 |
|  | MEM0903 | 0.947 | 0.004 | 0.049 |
|  | MEM0904 | 0.974 | 0.002 | 0.024 |
|  | MEM0905 | 0.491 | 0.083 | 0.426 |
|  | MEM0024 | 0.516 | 0.079 | 0.405 |
|  | MEM0906 | 0.541 | 0.075 | 0.384 |

TABLE 21

Isopropyl Myristate

| T80:TriAc | ID | Water | Oil | Surfactant |
|---|---|---|---|---|
| 4 to 1 | MEM0907 | 0.486 | 0.041 | 0.472 |
|  | MEM0908 | 0.511 | 0.039 | 0.449 |
|  | MEM0909 | 0.537 | 0.037 | 0.426 |
|  | MEM0910 | 0.562 | 0.035 | 0.403 |
|  | MEM0911 | 0.587 | 0.033 | 0.380 |
|  | MEM0912 | 0.612 | 0.031 | 0.357 |
|  | MEM0913 | 0.638 | 0.029 | 0.333 |
|  | MEM0914 | 0.663 | 0.027 | 0.310 |
|  | MEM0915 | 0.688 | 0.025 | 0.286 |
|  | MEM0916 | 0.714 | 0.023 | 0.263 |
|  | MEM0917 | 0.740 | 0.021 | 0.239 |

TABLE 21-continued

Isopropyl Myristate

| T80:TriAc | ID | Water | Oil | Surfactant |
|---|---|---|---|---|
| | MEM0918 | 0.765 | 0.019 | 0.216 |
| | MEM0919 | 0.791 | 0.017 | 0.192 |
| | MEM0920 | 0.817 | 0.015 | 0.168 |
| | MEM0921 | 0.843 | 0.013 | 0.144 |
| | MEM0922 | 0.869 | 0.011 | 0.121 |
| | MEM0923 | 0.895 | 0.008 | 0.097 |
| | MEM0924 | 0.921 | 0.006 | 0.073 |
| | MEM0925 | 0.947 | 0.004 | 0.048 |
| | MEM0926 | 0.974 | 0.002 | 0.024 |

TABLE 22

Isopropyl Myristate

| T80:TriAc | ID | Water | Oil | Surfactant |
|---|---|---|---|---|
| 5 to 1 | MEM0927 | 0.487 | 0.041 | 0.471 |
| | MEM0928 | 0.512 | 0.039 | 0.448 |
| | MEM0929 | 0.537 | 0.037 | 0.425 |
| | MEM0930 | 0.562 | 0.035 | 0.402 |
| | MEM0931 | 0.588 | 0.033 | 0.379 |
| | MEM0932 | 0.613 | 0.031 | 0.356 |
| | MEM0933 | 0.638 | 0.029 | 0.333 |
| | MEM0934 | 0.664 | 0.027 | 0.309 |
| | MEM0935 | 0.689 | 0.025 | 0.286 |
| | MEM0936 | 0.715 | 0.023 | 0.262 |
| | MEM0937 | 0.740 | 0.021 | 0.239 |
| | MEM0938 | 0.766 | 0.019 | 0.215 |
| | MEM0939 | 0.792 | 0.017 | 0.192 |
| | MEM0940 | 0.817 | 0.015 | 0.168 |
| | MEM0941 | 0.843 | 0.013 | 0.144 |
| | MEM0942 | 0.869 | 0.011 | 0.120 |
| | MEM0943 | 0.895 | 0.008 | 0.096 |
| | MEM0944 | 0.921 | 0.006 | 0.072 |
| | MEM0945 | 0.947 | 0.004 | 0.048 |
| | MEM0946 | 0.974 | 0.002 | 0.024 |

TABLE 23

Isopropyl Myristate

| CEL:TriAc | ID | Water | Oil | Surfactant |
|---|---|---|---|---|
| 3 to 1 | MEM1009 | 0.588 | 0.033 | 0.379 |
| | MEM1010 | 0.613 | 0.031 | 0.356 |
| | MEM1011 | 0.638 | 0.029 | 0.333 |
| | MEM1012 | 0.664 | 0.027 | 0.309 |
| | MEM1013 | 0.689 | 0.025 | 0.286 |
| | MEM1014 | 0.715 | 0.023 | 0.262 |
| | MEM1015 | 0.740 | 0.021 | 0.239 |
| | MEM1016 | 0.766 | 0.019 | 0.215 |
| | MEM1017 | 0.792 | 0.017 | 0.192 |
| | MEM1018 | 0.817 | 0.015 | 0.168 |
| | MEM1019 | 0.843 | 0.013 | 0.144 |
| | MEM1020 | 0.869 | 0.011 | 0.120 |
| | MEM1021 | 0.895 | 0.008 | 0.096 |
| | MEM1022 | 0.921 | 0.006 | 0.072 |
| | MEM1023 | 0.947 | 0.004 | 0.048 |
| | MEM1024 | 0.974 | 0.002 | 0.024 |
| | MEM0032 | 0.618 | 0.063 | 0.319 |
| | MEM1025 | 0.643 | 0.059 | 0.298 |
| | MEM1026 | 0.668 | 0.055 | 0.277 |
| | MEM1027 | 0.694 | 0.051 | 0.256 |
| | MEM1028 | 0.719 | 0.046 | 0.235 |
| | MEM1029 | 0.744 | 0.042 | 0.213 |
| | MEM1030 | 0.770 | 0.038 | 0.192 |
| | MEM1031 | 0.795 | 0.034 | 0.171 |
| | MEM1032 | 0.821 | 0.030 | 0.150 |
| | MEM1033 | 0.846 | 0.025 | 0.128 |
| | MEM1034 | 0.872 | 0.021 | 0.107 |
| | MEM1035 | 0.897 | 0.017 | 0.086 |

TABLE 23-continued

Isopropyl Myristate

| CEL:TriAc | ID | Water | Oil | Surfactant |
|---|---|---|---|---|
| | MEM1036 | 0.923 | 0.013 | 0.064 |
| | MEM1037 | 0.949 | 0.008 | 0.043 |
| | MEM1038 | 0.974 | 0.004 | 0.021 |

TABLE 24

Isopropyl Myristate

| CEL:P | ID | Water | Oil | Surfactant |
|---|---|---|---|---|
| 2 to 1 | MEM0022 | 0.081 | 0.077 | 0.842 |
| | MEM1039 | 0.494 | 0.042 | 0.464 |
| | MEM0016 | 0.503 | 0.039 | 0.458 |
| | MEM1040 | 0.519 | 0.040 | 0.441 |
| | MEM1041 | 0.544 | 0.038 | 0.418 |
| | MEM1042 | 0.569 | 0.036 | 0.395 |
| | MEM1043 | 0.594 | 0.034 | 0.372 |
| | MEM1044 | 0.619 | 0.032 | 0.349 |
| | MEM1045 | 0.644 | 0.029 | 0.326 |
| | MEM1046 | 0.669 | 0.027 | 0.303 |
| | MEM1047 | 0.695 | 0.025 | 0.280 |
| | MEM1048 | 0.720 | 0.023 | 0.257 |
| | MEM1049 | 0.745 | 0.021 | 0.234 |
| | MEM0010 | 0.771 | 0.019 | 0.210 |
| | MEM1050 | 0.796 | 0.017 | 0.187 |
| | MEM1051 | 0.821 | 0.015 | 0.164 |
| | MEM1052 | 0.847 | 0.013 | 0.141 |
| | MEM1053 | 0.872 | 0.011 | 0.117 |
| | MEM1054 | 0.898 | 0.008 | 0.094 |
| | MEM1055 | 0.923 | 0.006 | 0.070 |
| | MEM1056 | 0.949 | 0.004 | 0.047 |
| | MEM1057 | 0.974 | 0.002 | 0.024 |

TABLE 25

Isopropyl Myristate

| CEL:P | ID | Water | Oil | Surfactant |
|---|---|---|---|---|
| 3 to 1 | MEM1058 | 0.669 | 0.027 | 0.303 |
| | MEM1059 | 0.694 | 0.025 | 0.280 |
| | MEM1060 | 0.720 | 0.023 | 0.257 |
| | MEM1061 | 0.745 | 0.021 | 0.234 |
| | MEM1062 | 0.770 | 0.019 | 0.211 |
| | MEM1063 | 0.796 | 0.017 | 0.187 |
| | MEM1064 | 0.821 | 0.015 | 0.164 |
| | MEM1065 | 0.847 | 0.013 | 0.141 |
| | MEM1066 | 0.872 | 0.011 | 0.117 |
| | MEM1067 | 0.898 | 0.008 | 0.094 |
| | MEM1068 | 0.923 | 0.006 | 0.070 |
| | MEM1069 | 0.949 | 0.004 | 0.047 |
| | MEM1070 | 0.974 | 0.002 | 0.024 |

TABLE 26

Isopropyl Myristate

| CEL:P | ID | Water | Oil | Surfactant |
|---|---|---|---|---|
| 4 to 1 | MEM1071 | 0.669 | 0.027 | 0.304 |
| | MEM1072 | 0.694 | 0.025 | 0.280 |
| | MEM1073 | 0.720 | 0.023 | 0.257 |
| | MEM1074 | 0.745 | 0.021 | 0.234 |
| | MEM1075 | 0.770 | 0.019 | 0.211 |
| | MEM1076 | 0.796 | 0.017 | 0.187 |
| | MEM1077 | 0.821 | 0.015 | 0.164 |
| | MEM1078 | 0.847 | 0.013 | 0.141 |
| | MEM1079 | 0.872 | 0.011 | 0.117 |
| | MEM1080 | 0.898 | 0.008 | 0.094 |

TABLE 26-continued

Isopropyl Myristate

| CEL:P | ID | Water | Oil | Surfactant |
|---|---|---|---|---|
| | MEM1081 | 0.923 | 0.006 | 0.071 |
| | MEM1082 | 0.949 | 0.004 | 0.047 |
| | MEM1083 | 0.974 | 0.002 | 0.024 |
| | MEM1084 | 0.548 | 0.076 | 0.376 |
| | MEM1085 | 0.573 | 0.072 | 0.355 |
| | MEM0031 | 0.598 | 0.068 | 0.334 |
| | MEM1086 | 0.623 | 0.064 | 0.313 |
| | MEM1087 | 0.648 | 0.059 | 0.292 |
| | MEM1088 | 0.673 | 0.055 | 0.272 |
| | MEM1089 | 0.698 | 0.051 | 0.251 |
| | MEM1090 | 0.723 | 0.047 | 0.230 |
| | MEM1091 | 0.749 | 0.042 | 0.209 |
| | MEM1092 | 0.774 | 0.038 | 0.188 |
| | MEM1093 | 0.799 | 0.034 | 0.167 |
| | MEM1094 | 0.824 | 0.030 | 0.146 |
| | MEM1095 | 0.849 | 0.025 | 0.126 |
| | MEM1096 | 0.874 | 0.021 | 0.105 |
| | MEM1097 | 0.899 | 0.017 | 0.084 |
| | MEM1098 | 0.924 | 0.013 | 0.063 |
| | MEM1099 | 0.950 | 0.008 | 0.042 |
| | MEM1100 | 0.975 | 0.004 | 0.021 |

Example 3

Microemulsion Formulations Comprised of Isopropyl Palmitate

Tables 27-45 present representative formulations of microemulsions comprised of isopropyl palmitate and pairs of surfactants selected from Tween® 20 ("T20"), Tween® 80 ("T80"), polypropylene glycol ("P"), and glycerol ("G"). Numerical values are given as percent (w/w). "Surfactant" represents the percent (w/w) of total surfactant in each formulation.

TABLE 27

Isopropyl Palmitate

| T20:T80 | ID | Water | Oil | Surfactant |
|---|---|---|---|---|
| 1 to 1 | MEM0147 | 0.486 | 0.041 | 0.472 |
| | MEM0148 | 0.511 | 0.039 | 0.449 |
| | MEM0149 | 0.536 | 0.037 | 0.426 |
| | MEM0150 | 0.561 | 0.035 | 0.403 |
| | MEM0151 | 0.587 | 0.033 | 0.380 |
| | MEM0152 | 0.612 | 0.031 | 0.357 |

MEM0147-MEM0152 were unstable.

TABLE 28

Isopropyl Palmitate

| T20:T80 | ID | Water | Oil | Surfactant |
|---|---|---|---|---|
| 2 to 1 | MEM0153 | 0.485 | 0.041 | 0.474 |
| | MEM0154 | 0.510 | 0.039 | 0.451 |

MEM0153 and MEM0154 were unstable.

TABLE 29

Isopropyl Palmitate

| T20:T80 | ID | Water | Oil | Surfactant |
|---|---|---|---|---|
| 3 to 1 | MEM0155 | 0.484 | 0.041 | 0.475 |
| | MEM0156 | 0.509 | 0.039 | 0.452 |

TABLE 29-continued

Isopropyl Palmitate

| T20:T80 | ID | Water | Oil | Surfactant |
|---|---|---|---|---|
| | MEM0157 | 0.534 | 0.037 | 0.429 |
| | MEM0030 | 0.559 | 0.035 | 0.406 |
| | MEM0158 | 0.585 | 0.033 | 0.382 |
| | MEM0159 | 0.610 | 0.031 | 0.359 |

TABLE 30

Isopropyl Palmitate

| T20:T80 | ID | Water | Oil | Surfactant |
|---|---|---|---|---|
| 4 to 1 | MEM0160 | 0.484 | 0.041 | 0.475 |
| | MEM0161 | 0.509 | 0.039 | 0.452 |
| | MEM0162 | 0.534 | 0.037 | 0.429 |
| | MEM0163 | 0.559 | 0.035 | 0.406 |
| | MEM0164 | 0.584 | 0.033 | 0.383 |
| | MEM0165 | 0.978 | 0.019 | 0.003 |

TABLE 31

Isopropyl Palmitate

| T20:T80 | ID | Water | Oil | Surfactant |
|---|---|---|---|---|
| 5 to 1 | MEM0166 | 0.483 | 0.041 | 0.475 |
| | MEM0167 | 0.508 | 0.039 | 0.452 |
| | MEM0168 | 0.978 | 0.019 | 0.003 |
| | MEM0169 | 0.973 | 0.002 | 0.025 |

TABLE 32

Isopropyl Palmitate

| T20:T80 | ID | Water | Oil | Surfactant |
|---|---|---|---|---|
| 1 to 2 | MEM0170 | 0.488 | 0.042 | 0.471 |
| | MEM0171 | 0.513 | 0.040 | 0.448 |
| | MEM0172 | 0.538 | 0.038 | 0.425 |
| | MEM0173 | 0.563 | 0.035 | 0.402 |
| | MEM0174 | 0.588 | 0.033 | 0.379 |
| | MEM0175 | 0.613 | 0.031 | 0.355 |
| | MEM0176 | 0.639 | 0.029 | 0.332 |
| | MEM0177 | 0.664 | 0.027 | 0.309 |
| | MEM0178 | 0.689 | 0.025 | 0.285 |
| | MEM0179 | 0.948 | 0.004 | 0.048 |
| | MEM0180 | 0.974 | 0.002 | 0.024 |

MEM0170-MEM0175 were unstable.

TABLE 33

Isopropyl Palmitate

| T20:T80 | ID | Water | Oil | Surfactant |
|---|---|---|---|---|
| 1 to 3 | MEM0181 | 0.488 | 0.042 | 0.470 |
| | MEM0182 | 0.513 | 0.040 | 0.447 |
| | MEM0183 | 0.538 | 0.038 | 0.424 |
| | MEM0184 | 0.563 | 0.036 | 0.401 |
| | MEM0185 | 0.589 | 0.033 | 0.378 |
| | MEM0186 | 0.614 | 0.031 | 0.355 |
| | MEM0187 | 0.639 | 0.029 | 0.331 |
| | MEM0188 | 0.665 | 0.027 | 0.308 |
| | MEM0189 | 0.690 | 0.025 | 0.285 |
| | MEM0190 | 0.716 | 0.023 | 0.261 |
| | MEM0191 | 0.741 | 0.021 | 0.238 |
| | MEM0192 | 0.767 | 0.019 | 0.214 |
| | MEM0193 | 0.792 | 0.017 | 0.191 |

TABLE 33-continued

Isopropyl Palmitate

| T20:T80 | ID | Water | Oil | Surfactant |
|---|---|---|---|---|
| | MEM0194 | 0.818 | 0.015 | 0.167 |
| | MEM0195 | 0.844 | 0.013 | 0.143 |
| | MEM0196 | 0.870 | 0.011 | 0.120 |
| | MEM0197 | 0.896 | 0.008 | 0.096 |
| | MEM0198 | 0.922 | 0.006 | 0.072 |
| | MEM0199 | 0.948 | 0.004 | 0.048 |
| | MEM0200 | 0.974 | 0.002 | 0.024 |
| | MEM0201 | 0.974 | 0.004 | 0.021 |

MEM018-MEM0187 were unstable.

TABLE 34

Isopropyl Palmitate

| T20:T80 | ID | Water | Oil | Surfactant |
|---|---|---|---|---|
| 1 to 4 | MEM0202 | 0.489 | 0.042 | 0.470 |
| | MEM0203 | 0.514 | 0.040 | 0.447 |
| | MEM0204 | 0.539 | 0.038 | 0.424 |
| | MEM0205 | 0.564 | 0.036 | 0.401 |
| | MEM0206 | 0.589 | 0.033 | 0.377 |
| | MEM0207 | 0.614 | 0.031 | 0.354 |
| | MEM0208 | 0.640 | 0.029 | 0.331 |
| | MEM0209 | 0.665 | 0.027 | 0.308 |
| | MEM0210 | 0.690 | 0.025 | 0.284 |
| | MEM0211 | 0.716 | 0.023 | 0.261 |
| | MEM0212 | 0.741 | 0.021 | 0.238 |
| | MEM0213 | 0.767 | 0.019 | 0.214 |
| | MEM0214 | 0.793 | 0.017 | 0.190 |
| | MEM0215 | 0.818 | 0.015 | 0.167 |
| | MEM0216 | 0.844 | 0.013 | 0.143 |
| | MEM0217 | 0.870 | 0.011 | 0.119 |
| | MEM0218 | 0.896 | 0.008 | 0.096 |
| | MEM0219 | 0.922 | 0.006 | 0.072 |
| | MEM0220 | 0.948 | 0.004 | 0.048 |
| | MEM0221 | 0.974 | 0.002 | 0.024 |
| | MEM0222 | 0.974 | 0.004 | 0.021 |

MEM0202-MEM0208 were unstable.

TABLE 35

Isopropyl Palmitate

| T20:T80 | ID | Water | Oil | Surfactant |
|---|---|---|---|---|
| 1 to 5 | MEM0223 | 0.489 | 0.042 | 0.469 |
| | MEM0224 | 0.514 | 0.040 | 0.446 |
| | MEM0225 | 0.539 | 0.038 | 0.423 |
| | MEM0226 | 0.564 | 0.036 | 0.400 |
| | MEM0227 | 0.589 | 0.034 | 0.377 |
| | MEM0228 | 0.615 | 0.031 | 0.354 |
| | MEM0229 | 0.640 | 0.029 | 0.331 |
| | MEM0230 | 0.665 | 0.027 | 0.307 |
| | MEM0231 | 0.691 | 0.025 | 0.284 |
| | MEM0232 | 0.716 | 0.023 | 0.261 |
| | MEM0233 | 0.742 | 0.021 | 0.237 |
| | MEM0234 | 0.767 | 0.019 | 0.214 |
| | MEM0235 | 0.793 | 0.017 | 0.190 |
| | MEM0236 | 0.819 | 0.015 | 0.167 |
| | MEM0237 | 0.844 | 0.013 | 0.143 |
| | MEM0238 | 0.870 | 0.011 | 0.119 |
| | MEM0239 | 0.896 | 0.008 | 0.096 |
| | MEM0240 | 0.922 | 0.006 | 0.072 |
| | MEM0241 | 0.948 | 0.004 | 0.048 |
| | MEM0242 | 0.974 | 0.002 | 0.024 |
| | MEM0243 | 0.974 | 0.004 | 0.021 |

MEM0223-MEM0230 were unstable.

TABLE 36

Isopropyl Palmitate

| T80:P | ID | Water | Oil | Surfactant |
|---|---|---|---|---|
| 1 to 1 | MEM0427 | 0.846 | 0.013 | 0.141 |
| | MEM0428 | 0.872 | 0.011 | 0.117 |
| | MEM0429 | 0.897 | 0.009 | 0.094 |
| | MEM0430 | 0.923 | 0.006 | 0.071 |
| | MEM0431 | 0.949 | 0.004 | 0.047 |
| | MEM0432 | 0.974 | 0.002 | 0.024 |

TABLE 37

Isopropyl Palmitate

| T80:P | ID | Water | Oil | Surfactant |
|---|---|---|---|---|
| 2 to 1 | MEM0433 | 0.492 | 0.042 | 0.466 |
| | MEM0434 | 0.542 | 0.038 | 0.420 |
| | MEM0435 | 0.592 | 0.034 | 0.374 |
| | MEM0436 | 0.948 | 0.004 | 0.047 |
| | MEM0437 | 0.974 | 0.002 | 0.024 |
| | MEM0438 | 0.975 | 0.004 | 0.021 |

TABLE 38

Isopropyl Palmitate

| T80:P | ID | Water | Oil | Surfactant |
|---|---|---|---|---|
| 3 to 1 | MEM0439 | 0.492 | 0.042 | 0.466 |
| | MEM0440 | 0.517 | 0.040 | 0.443 |
| | MEM0441 | 0.542 | 0.038 | 0.420 |
| | MEM0442 | 0.567 | 0.036 | 0.397 |
| | MEM0443 | 0.592 | 0.034 | 0.374 |
| | MEM0444 | 0.617 | 0.032 | 0.351 |
| | MEM0445 | 0.642 | 0.029 | 0.328 |
| | MEM0446 | 0.693 | 0.025 | 0.282 |
| | MEM0447 | 0.795 | 0.017 | 0.188 |
| | MEM0448 | 0.846 | 0.013 | 0.142 |
| | MEM0449 | 0.871 | 0.011 | 0.118 |
| | MEM0450 | 0.897 | 0.008 | 0.095 |
| | MEM0451 | 0.923 | 0.006 | 0.071 |
| | MEM0452 | 0.948 | 0.004 | 0.047 |
| | MEM0453 | 0.974 | 0.002 | 0.024 |
| | MEM0454 | 0.924 | 0.013 | 0.063 |
| | MEM0455 | 0.949 | 0.009 | 0.042 |
| | MEM0456 | 0.975 | 0.004 | 0.021 |

TABLE 39

Isopropyl Palmitate

| T80:P | ID | Water | Oil | Surfactant |
|---|---|---|---|---|
| 4 to 1 | MEM0041 | 0.491 | 0.042 | 0.467 |
| | MEM0457 | 0.516 | 0.040 | 0.444 |
| | MEM0458 | 0.542 | 0.038 | 0.421 |
| | MEM0459 | 0.567 | 0.036 | 0.398 |
| | MEM0460 | 0.592 | 0.034 | 0.375 |
| | MEM0461 | 0.617 | 0.032 | 0.352 |
| | MEM0462 | 0.642 | 0.029 | 0.328 |
| | MEM0463 | 0.820 | 0.015 | 0.165 |
| | MEM0464 | 0.846 | 0.013 | 0.142 |
| | MEM0465 | 0.871 | 0.011 | 0.118 |
| | MEM0466 | 0.897 | 0.008 | 0.095 |
| | MEM0467 | 0.923 | 0.006 | 0.071 |
| | MEM0468 | 0.948 | 0.004 | 0.047 |
| | MEM0469 | 0.974 | 0.002 | 0.024 |

TABLE 40

Isopropyl Palmitate

| T80:P | ID | Water | Oil | Surfactant |
|---|---|---|---|---|
| 5 to 1 | MEM0470 | 0.491 | 0.042 | 0.467 |
|  | MEM0471 | 0.516 | 0.040 | 0.444 |
|  | MEM0472 | 0.541 | 0.038 | 0.421 |
|  | MEM0473 | 0.566 | 0.036 | 0.398 |
|  | MEM0474 | 0.592 | 0.034 | 0.375 |
|  | MEM0475 | 0.617 | 0.032 | 0.352 |
|  | MEM0476 | 0.642 | 0.029 | 0.329 |
|  | MEM0477 | 0.667 | 0.027 | 0.305 |
|  | MEM0478 | 0.693 | 0.025 | 0.282 |
|  | MEM0479 | 0.718 | 0.023 | 0.259 |
|  | MEM0480 | 0.743 | 0.021 | 0.235 |
|  | MEM0481 | 0.769 | 0.019 | 0.212 |
|  | MEM0482 | 0.794 | 0.017 | 0.189 |
|  | MEM0483 | 0.820 | 0.015 | 0.165 |
|  | MEM0484 | 0.845 | 0.013 | 0.142 |
|  | MEM0485 | 0.871 | 0.011 | 0.118 |
|  | MEM0486 | 0.897 | 0.008 | 0.095 |
|  | MEM0487 | 0.923 | 0.006 | 0.071 |
|  | MEM0488 | 0.948 | 0.004 | 0.047 |
|  | MEM0489 | 0.974 | 0.002 | 0.024 |
|  | MEM0490 | 0.848 | 0.026 | 0.126 |
|  | MEM0491 | 0.873 | 0.021 | 0.105 |
|  | MEM0492 | 0.899 | 0.017 | 0.084 |
|  | MEM0493 | 0.924 | 0.013 | 0.063 |
|  | MEM0494 | 0.949 | 0.009 | 0.042 |
|  | MEM0495 | 0.975 | 0.004 | 0.021 |
|  | MEM0496 | 0.900 | 0.026 | 0.074 |
|  | MEM0497 | 0.925 | 0.019 | 0.055 |
|  | MEM0498 | 0.950 | 0.013 | 0.037 |
|  | MEM0499 | 0.975 | 0.006 | 0.018 |

MEM0470-MEM0473 were unstable.

TABLE 41

Isopropyl Palmitate

| T80:G | ID | Water | Oil | Surfactant |
|---|---|---|---|---|
| 1 to 1 | MEM0623 | 0.472 | 0.040 | 0.488 |
|  | MEM0035 | 0.497 | 0.038 | 0.464 |
|  | MEM0624 | 0.522 | 0.036 | 0.441 |
|  | MEM0625 | 0.944 | 0.004 | 0.051 |
|  | MEM0626 | 0.972 | 0.002 | 0.026 |

TABLE 42

Isopropyl Palmitate

| T80:G | ID | Water | Oil | Surfactant |
|---|---|---|---|---|
| 2 to 1 | MEM0036 | 0.478 | 0.041 | 0.481 |
|  | MEM0037 | 0.503 | 0.039 | 0.458 |
|  | MEM0627 | 0.529 | 0.037 | 0.435 |
|  | MEM0628 | 0.554 | 0.035 | 0.411 |
|  | MEM0629 | 0.579 | 0.033 | 0.388 |
|  | MEM0630 | 0.605 | 0.031 | 0.365 |
|  | MEM0631 | 0.630 | 0.029 | 0.341 |
|  | MEM0632 | 0.656 | 0.027 | 0.317 |
|  | MEM0633 | 0.733 | 0.021 | 0.246 |
|  | MEM0634 | 0.760 | 0.019 | 0.222 |
|  | MEM0635 | 0.786 | 0.017 | 0.197 |

TABLE 43

Isopropyl Palmitate

| T80:G | ID | Water | Oil | Surfactant |
|---|---|---|---|---|
| 3 to 1 | MEM0038 | 0.481 | 0.041 | 0.477 |
|  | MEM0636 | 0.506 | 0.039 | 0.454 |

TABLE 43-continued

Isopropyl Palmitate

| T80:G | ID | Water | Oil | Surfactant |
|---|---|---|---|---|
|  | MEM0637 | 0.532 | 0.037 | 0.431 |
|  | MEM0638 | 0.557 | 0.035 | 0.408 |
|  | MEM0639 | 0.582 | 0.033 | 0.385 |
|  | MEM0640 | 0.607 | 0.031 | 0.361 |
|  | MEM0641 | 0.633 | 0.029 | 0.338 |
|  | MEM0642 | 0.659 | 0.027 | 0.314 |
|  | MEM0643 | 0.684 | 0.025 | 0.291 |
|  | MEM0644 | 0.736 | 0.021 | 0.243 |
|  | MEM0645 | 0.762 | 0.019 | 0.219 |
|  | MEM0646 | 0.788 | 0.017 | 0.195 |
|  | MEM0647 | 0.814 | 0.015 | 0.171 |
|  | MEM0648 | 0.840 | 0.013 | 0.147 |
|  | MEM0649 | 0.867 | 0.011 | 0.123 |
|  | MEM0650 | 0.893 | 0.008 | 0.098 |
|  | MEM0651 | 0.920 | 0.006 | 0.074 |
|  | MEM0652 | 0.895 | 0.017 | 0.088 |
|  | MEM0653 | 0.921 | 0.013 | 0.066 |
|  | MEM0654 | 0.948 | 0.009 | 0.044 |
|  | MEM0655 | 0.974 | 0.004 | 0.022 |

TABLE 44

Isopropyl Palmitate

| T80:G | ID | Water | Oil | Surfactant |
|---|---|---|---|---|
| 4 to 1 | MEM0656 | 0.483 | 0.041 | 0.476 |
|  | MEM0657 | 0.508 | 0.039 | 0.452 |
|  | MEM0658 | 0.533 | 0.037 | 0.429 |
|  | MEM0659 | 0.559 | 0.035 | 0.406 |
|  | MEM0660 | 0.584 | 0.033 | 0.383 |
|  | MEM0661 | 0.609 | 0.031 | 0.360 |
|  | MEM0662 | 0.635 | 0.029 | 0.336 |
|  | MEM0663 | 0.660 | 0.027 | 0.313 |
|  | MEM0664 | 0.686 | 0.025 | 0.289 |
|  | MEM0665 | 0.711 | 0.023 | 0.266 |
|  | MEM0666 | 0.737 | 0.021 | 0.242 |
|  | MEM0667 | 0.763 | 0.019 | 0.218 |
|  | MEM0668 | 0.789 | 0.017 | 0.194 |
|  | MEM0669 | 0.815 | 0.015 | 0.170 |
|  | MEM0670 | 0.841 | 0.013 | 0.146 |
|  | MEM0671 | 0.868 | 0.011 | 0.122 |
|  | MEM0672 | 0.894 | 0.008 | 0.098 |
|  | MEM0673 | 0.920 | 0.006 | 0.073 |
|  | MEM0674 | 0.947 | 0.004 | 0.049 |
|  | MEM0675 | 0.973 | 0.002 | 0.025 |
|  | MEM0676 | 0.665 | 0.055 | 0.280 |
|  | MEM0677 | 0.691 | 0.050 | 0.259 |
|  | MEM0678 | 0.716 | 0.046 | 0.238 |
|  | MEM0679 | 0.742 | 0.042 | 0.216 |
|  | MEM0680 | 0.767 | 0.038 | 0.195 |
|  | MEM0681 | 0.793 | 0.034 | 0.173 |
|  | MEM0682 | 0.819 | 0.030 | 0.152 |
|  | MEM0683 | 0.844 | 0.025 | 0.130 |
|  | MEM0684 | 0.870 | 0.021 | 0.109 |
|  | MEM0685 | 0.896 | 0.017 | 0.087 |
|  | MEM0686 | 0.922 | 0.013 | 0.065 |
|  | MEM0687 | 0.948 | 0.009 | 0.044 |
|  | MEM0688 | 0.974 | 0.004 | 0.022 |

TABLE 45

Isopropyl Palmitate

| T80:G | ID | Water | Oil | Surfactant |
|---|---|---|---|---|
| 5 to 1 | MEM0689 | 0.484 | 0.041 | 0.474 |
|  | MEM0690 | 0.509 | 0.039 | 0.451 |
|  | MEM0691 | 0.535 | 0.037 | 0.428 |
|  | MEM0692 | 0.560 | 0.035 | 0.405 |
|  | MEM0693 | 0.585 | 0.033 | 0.382 |

TABLE 45-continued

Isopropyl Palmitate

| T80:G | ID | Water | Oil | Surfactant |
|---|---|---|---|---|
| | MEM0694 | 0.610 | 0.031 | 0.358 |
| | MEM0695 | 0.636 | 0.029 | 0.335 |
| | MEM0696 | 0.661 | 0.027 | 0.312 |
| | MEM0697 | 0.687 | 0.025 | 0.288 |
| | MEM0698 | 0.712 | 0.023 | 0.265 |
| | MEM0699 | 0.738 | 0.021 | 0.241 |
| | MEM0700 | 0.764 | 0.019 | 0.217 |
| | MEM0701 | 0.790 | 0.017 | 0.193 |
| | MEM0702 | 0.816 | 0.015 | 0.169 |
| | MEM0703 | 0.842 | 0.013 | 0.145 |
| | MEM0704 | 0.868 | 0.011 | 0.121 |
| | MEM0705 | 0.894 | 0.008 | 0.097 |
| | MEM0706 | 0.921 | 0.006 | 0.073 |
| | MEM0707 | 0.947 | 0.004 | 0.049 |
| | MEM0708 | 0.973 | 0.002 | 0.024 |
| | MEM0709 | 0.666 | 0.055 | 0.279 |
| | MEM0710 | 0.692 | 0.051 | 0.258 |
| | MEM0711 | 0.717 | 0.046 | 0.237 |
| | MEM0712 | 0.742 | 0.042 | 0.215 |
| | MEM0713 | 0.768 | 0.038 | 0.194 |
| | MEM0714 | 0.794 | 0.034 | 0.173 |
| | MEM0715 | 0.819 | 0.030 | 0.151 |
| | MEM0716 | 0.845 | 0.025 | 0.130 |
| | MEM0717 | 0.871 | 0.021 | 0.108 |
| | MEM0718 | 0.896 | 0.017 | 0.087 |
| | MEM0719 | 0.922 | 0.013 | 0.065 |
| | MEM0720 | 0.948 | 0.009 | 0.043 |
| | MEM0721 | 0.974 | 0.004 | 0.022 |

Example 4

Microemulsion Formulations Comprised of Medium Chain Triglyceride

Tables 46-68 present representative formulations of microemulsions comprised of medium chain triglyceride ("MCT") and pairs of surfactants selected from Tween® 20 ("T20"), Tween® 80 ("T80"), polypropylene glycol ("P"), glycerol ("G"), triacetin ("TriAc"), and Cremophor® EL ("CEL"). Numerical values are given as percent (w/w). "Surfactant" represents the percent (w/w) of total surfactant in each formulation.

TABLE 46

MCT

| T20:T80 | ID | Water | Oil | Surfactant |
|---|---|---|---|---|
| 1 to 1 | MEM0244 | 0.484 | 0.046 | 0.470 |
| | MEM0245 | 0.509 | 0.044 | 0.448 |
| | MEM0246 | 0.534 | 0.041 | 0.425 |
| | MEM0065 | 0.559 | 0.039 | 0.402 |
| | MEM0247 | 0.584 | 0.037 | 0.379 |
| | MEM0248 | 0.610 | 0.035 | 0.356 |
| | MEM0066 | 0.635 | 0.032 | 0.332 |
| | MEM0249 | 0.661 | 0.030 | 0.309 |
| | MEM0067 | 0.686 | 0.028 | 0.286 |
| | MEM0250 | 0.712 | 0.026 | 0.262 |
| | MEM0251 | 0.738 | 0.023 | 0.239 |
| | MEM0252 | 0.764 | 0.021 | 0.215 |
| | MEM0253 | 0.789 | 0.019 | 0.192 |
| | MEM0254 | 0.816 | 0.016 | 0.168 |
| | MEM0255 | 0.842 | 0.014 | 0.144 |
| | MEM0256 | 0.920 | 0.007 | 0.073 |
| | MEM0257 | 0.973 | 0.002 | 0.024 |
| | MEM0258 | 0.976 | 0.021 | 0.003 |

TABLE 47

MCT

| T20:T80 | ID | Water | Oil | Surfactant |
|---|---|---|---|---|
| 2 to 1 | MEM0259 | 0.483 | 0.046 | 0.472 |
| | MEM0260 | 0.508 | 0.043 | 0.449 |
| | MEM0261 | 0.973 | 0.002 | 0.024 |
| | MEM0262 | 0.928 | 0.064 | 0.008 |
| | MEM0263 | 0.952 | 0.043 | 0.005 |
| | MEM0264 | 0.976 | 0.021 | 0.003 |

MEM0259 and MEM0260 were unstable.

TABLE 48

MCT

| T20:T80 | ID | Water | Oil | Surfactant |
|---|---|---|---|---|
| 3 to 1 | MEM0265 | 0.482 | 0.046 | 0.473 |
| | MEM0266 | 0.507 | 0.043 | 0.450 |
| | MEM0267 | 0.532 | 0.041 | 0.427 |
| | MEM0268 | 0.557 | 0.039 | 0.404 |
| | MEM0269 | 0.582 | 0.037 | 0.381 |
| | MEM0270 | 0.608 | 0.034 | 0.358 |
| | MEM0271 | 0.928 | 0.064 | 0.008 |
| | MEM0272 | 0.952 | 0.043 | 0.005 |
| | MEM0273 | 0.976 | 0.021 | 0.003 |

TABLE 49

MCT

| T20:T80 | ID | Water | Oil | Surfactant |
|---|---|---|---|---|
| 4 to 1 | MEM0274 | 0.946 | 0.005 | 0.049 |
| | MEM0275 | 0.973 | 0.002 | 0.025 |
| | MEM0276 | 0.904 | 0.085 | 0.010 |
| | MEM0277 | 0.928 | 0.064 | 0.008 |
| | MEM0278 | 0.952 | 0.043 | 0.005 |
| | MEM0279 | 0.976 | 0.021 | 0.003 |

TABLE 50

MCT

| T20:T80 | ID | Water | Oil | Surfactant |
|---|---|---|---|---|
| 5 to 1 | MEM0280 | 0.974 | 0.007 | 0.019 |
| | MEM0281 | 0.948 | 0.019 | 0.033 |
| | MEM0282 | 0.974 | 0.009 | 0.016 |
| | MEM0283 | 0.928 | 0.064 | 0.008 |
| | MEM0284 | 0.952 | 0.043 | 0.005 |
| | MEM0285 | 0.976 | 0.021 | 0.003 |

TABLE 51

MCT

| T20:T80 | ID | Water | Oil | Surfactant |
|---|---|---|---|---|
| 1 to 2 | MEM0286 | 0.485 | 0.046 | 0.469 |
| | MEM0287 | 0.510 | 0.044 | 0.446 |
| | MEM0288 | 0.535 | 0.041 | 0.423 |
| | MEM0289 | 0.561 | 0.039 | 0.400 |
| | MEM0290 | 0.586 | 0.037 | 0.377 |
| | MEM0291 | 0.611 | 0.035 | 0.354 |
| | MEM0292 | 0.637 | 0.032 | 0.331 |
| | MEM0293 | 0.662 | 0.030 | 0.308 |
| | MEM0068 | 0.688 | 0.028 | 0.285 |
| | MEM0069 | 0.713 | 0.026 | 0.261 |
| | MEM0294 | 0.739 | 0.023 | 0.238 |

TABLE 51-continued

| | | MCT | | |
|---|---|---|---|---|
| T20:T80 | ID | Water | Oil | Surfactant |
| | MEM0295 | 0.765 | 0.021 | 0.214 |
| | MEM0296 | 0.790 | 0.019 | 0.191 |
| | MEM0297 | 0.816 | 0.016 | 0.167 |
| | MEM0298 | 0.842 | 0.014 | 0.144 |
| | MEM0299 | 0.868 | 0.012 | 0.120 |
| | MEM0300 | 0.895 | 0.009 | 0.096 |
| | MEM0301 | 0.921 | 0.007 | 0.072 |
| | MEM0302 | 0.947 | 0.005 | 0.048 |
| | MEM0303 | 0.974 | 0.002 | 0.024 |

MEM0286-MEM0292 were unstable.

TABLE 52

| | | MCT | | |
|---|---|---|---|---|
| T20:T80 | ID | Water | Oil | Surfactant |
| 1 to 3 | MEM0304 | 0.486 | 0.046 | 0.468 |
| | MEM0305 | 0.511 | 0.044 | 0.445 |
| | MEM0070 | 0.536 | 0.041 | 0.422 |
| | MEM0306 | 0.561 | 0.039 | 0.400 |
| | MEM0071 | 0.587 | 0.037 | 0.377 |
| | MEM0072 | 0.612 | 0.035 | 0.354 |
| | MEM0307 | 0.637 | 0.032 | 0.330 |
| | MEM0308 | 0.663 | 0.030 | 0.307 |
| | MEM0309 | 0.688 | 0.028 | 0.284 |
| | MEM0310 | 0.714 | 0.026 | 0.261 |
| | MEM0311 | 0.739 | 0.023 | 0.237 |
| | MEM0312 | 0.765 | 0.021 | 0.214 |
| | MEM0313 | 0.791 | 0.019 | 0.190 |
| | MEM0314 | 0.817 | 0.016 | 0.167 |
| | MEM0315 | 0.843 | 0.014 | 0.143 |
| | MEM0316 | 0.869 | 0.012 | 0.120 |
| | MEM0317 | 0.895 | 0.009 | 0.096 |
| | MEM0318 | 0.921 | 0.007 | 0.072 |
| | MEM0319 | 0.947 | 0.005 | 0.048 |
| | MEM0320 | 0.974 | 0.002 | 0.024 |
| | MEM0321 | 0.793 | 0.037 | 0.170 |
| | MEM0322 | 0.819 | 0.033 | 0.149 |
| | MEM0323 | 0.844 | 0.028 | 0.128 |
| | MEM0324 | 0.974 | 0.005 | 0.021 |

MEM0304 and MEM0305 were unstable.

TABLE 53

| | | MCT | | |
|---|---|---|---|---|
| T20:T80 | ID | Water | Oil | Surfactant |
| 1 to 4 | MEM0325 | 0.486 | 0.046 | 0.468 |
| | MEM0326 | 0.511 | 0.044 | 0.445 |
| | MEM0327 | 0.537 | 0.041 | 0.422 |
| | MEM0328 | 0.562 | 0.039 | 0.399 |
| | MEM0329 | 0.587 | 0.037 | 0.376 |
| | MEM0073 | 0.612 | 0.035 | 0.353 |
| | MEM0074 | 0.638 | 0.032 | 0.330 |
| | MEM0075 | 0.663 | 0.030 | 0.307 |
| | MEM0076 | 0.688 | 0.028 | 0.284 |
| | MEM0330 | 0.714 | 0.026 | 0.260 |
| | MEM0331 | 0.740 | 0.023 | 0.237 |
| | MEM0332 | 0.765 | 0.021 | 0.214 |
| | MEM0333 | 0.791 | 0.019 | 0.190 |
| | MEM0334 | 0.817 | 0.016 | 0.167 |
| | MEM0335 | 0.843 | 0.014 | 0.143 |
| | MEM0336 | 0.869 | 0.012 | 0.119 |
| | MEM0337 | 0.895 | 0.009 | 0.096 |
| | MEM0338 | 0.921 | 0.007 | 0.072 |
| | MEM0339 | 0.947 | 0.005 | 0.048 |
| | MEM0340 | 0.974 | 0.002 | 0.024 |
| | MEM0341 | 0.793 | 0.037 | 0.169 |
| | MEM0342 | 0.819 | 0.033 | 0.148 |

TABLE 53-continued

| | | MCT | | |
|---|---|---|---|---|
| T20:T80 | ID | Water | Oil | Surfactant |
| | MEM0343 | 0.845 | 0.028 | 0.127 |
| | MEM0344 | 0.948 | 0.009 | 0.043 |
| | MEM0345 | 0.974 | 0.005 | 0.021 |

MEM0325-MEM0327 were unstable.

TABLE 54

| | | MCT | | |
|---|---|---|---|---|
| T20:T80 | ID | Water | Oil | Surfactant |
| 1 to 5 | MEM0346 | 0.487 | 0.046 | 0.467 |
| | MEM0347 | 0.512 | 0.044 | 0.444 |
| | MEM0348 | 0.537 | 0.042 | 0.422 |
| | MEM0349 | 0.562 | 0.039 | 0.399 |
| | MEM0350 | 0.587 | 0.037 | 0.376 |
| | MEM0351 | 0.613 | 0.035 | 0.353 |
| | MEM0352 | 0.638 | 0.032 | 0.330 |
| | MEM0077 | 0.663 | 0.030 | 0.306 |
| | MEM0353 | 0.689 | 0.028 | 0.283 |
| | MEM0354 | 0.714 | 0.026 | 0.260 |
| | MEM0355 | 0.740 | 0.023 | 0.237 |
| | MEM0356 | 0.766 | 0.021 | 0.213 |
| | MEM0357 | 0.791 | 0.019 | 0.190 |
| | MEM0358 | 0.817 | 0.016 | 0.166 |
| | MEM0359 | 0.843 | 0.014 | 0.143 |
| | MEM0360 | 0.869 | 0.012 | 0.119 |
| | MEM0361 | 0.895 | 0.009 | 0.095 |
| | MEM0362 | 0.921 | 0.007 | 0.072 |
| | MEM0363 | 0.947 | 0.005 | 0.048 |
| | MEM0364 | 0.974 | 0.002 | 0.024 |
| | MEM0365 | 0.641 | 0.065 | 0.294 |
| | MEM0366 | 0.666 | 0.061 | 0.273 |
| | MEM0367 | 0.691 | 0.056 | 0.253 |
| | MEM0368 | 0.717 | 0.051 | 0.232 |
| | MEM0369 | 0.742 | 0.047 | 0.211 |
| | MEM0370 | 0.768 | 0.042 | 0.190 |
| | MEM0371 | 0.793 | 0.037 | 0.169 |
| | MEM0372 | 0.819 | 0.033 | 0.148 |
| | MEM0373 | 0.845 | 0.028 | 0.127 |
| | MEM0374 | 0.948 | 0.009 | 0.043 |

MEM0346-MEM0352 were unstable.

TABLE 55

| | | MCT | | |
|---|---|---|---|---|
| T80:P | ID | Water | Oil | Surfactant |
| 2 to 1 | MEM0500 | 0.540 | 0.042 | 0.418 |
| | MEM0501 | 0.590 | 0.037 | 0.373 |
| | MEM0502 | 0.641 | 0.033 | 0.327 |
| | MEM0503 | 0.793 | 0.019 | 0.188 |
| | MEM0504 | 0.819 | 0.016 | 0.164 |
| | MEM0505 | 0.845 | 0.014 | 0.141 |
| | MEM0506 | 0.871 | 0.012 | 0.118 |
| | MEM0507 | 0.896 | 0.009 | 0.094 |
| | MEM0508 | 0.922 | 0.007 | 0.071 |
| | MEM0509 | 0.948 | 0.005 | 0.047 |
| | MEM0510 | 0.974 | 0.002 | 0.024 |

TABLE 56

| | | MCT | | |
|---|---|---|---|---|
| T80:P | ID | Water | Oil | Surfactant |
| 3 to 1 | MEM0511 | 0.489 | 0.046 | 0.464 |
| | MEM0512 | 0.514 | 0.044 | 0.442 |

TABLE 56-continued

| | | MCT | | |
|---|---|---|---|---|
| T80:P | ID | Water | Oil | Surfactant |
| | MEM0513 | 0.540 | 0.042 | 0.419 |
| | MEM0514 | 0.565 | 0.039 | 0.396 |
| | MEM0515 | 0.590 | 0.037 | 0.373 |
| | MEM0516 | 0.615 | 0.035 | 0.350 |
| | MEM0517 | 0.640 | 0.033 | 0.327 |
| | MEM0518 | 0.666 | 0.030 | 0.304 |
| | MEM0519 | 0.691 | 0.028 | 0.281 |
| | MEM0520 | 0.717 | 0.026 | 0.258 |
| | MEM0521 | 0.742 | 0.023 | 0.235 |
| | MEM0522 | 0.768 | 0.021 | 0.211 |
| | MEM0523 | 0.793 | 0.019 | 0.188 |
| | MEM0524 | 0.819 | 0.016 | 0.165 |
| | MEM0525 | 0.845 | 0.014 | 0.141 |
| | MEM0526 | 0.870 | 0.012 | 0.118 |
| | MEM0527 | 0.896 | 0.009 | 0.094 |
| | MEM0528 | 0.922 | 0.007 | 0.071 |
| | MEM0529 | 0.948 | 0.005 | 0.047 |
| | MEM0530 | 0.974 | 0.002 | 0.024 |

TABLE 57

| | | MCT | | |
|---|---|---|---|---|
| T80:P | ID | Water | Oil | Surfactant |
| 4 to 1 | MEM0531 | 0.489 | 0.046 | 0.465 |
| | MEM0532 | 0.514 | 0.044 | 0.442 |
| | MEM0533 | 0.539 | 0.042 | 0.419 |
| | MEM0534 | 0.564 | 0.039 | 0.396 |
| | MEM0535 | 0.590 | 0.037 | 0.373 |
| | MEM0536 | 0.615 | 0.035 | 0.350 |
| | MEM0537 | 0.640 | 0.033 | 0.327 |
| | MEM0538 | 0.691 | 0.028 | 0.281 |
| | MEM0539 | 0.716 | 0.026 | 0.258 |
| | MEM0540 | 0.742 | 0.023 | 0.235 |
| | MEM0541 | 0.767 | 0.021 | 0.212 |
| | MEM0542 | 0.793 | 0.019 | 0.188 |
| | MEM0543 | 0.819 | 0.016 | 0.165 |
| | MEM0544 | 0.844 | 0.014 | 0.142 |
| | MEM0545 | 0.870 | 0.012 | 0.118 |
| | MEM0546 | 0.896 | 0.009 | 0.095 |
| | MEM0547 | 0.922 | 0.007 | 0.071 |
| | MEM0548 | 0.948 | 0.005 | 0.047 |
| | MEM0549 | 0.974 | 0.002 | 0.024 |

TABLE 58

| | | MCT | | |
|---|---|---|---|---|
| T80:P | ID | Water | Oil | Surfactant |
| 5 to 1 | MEM0550 | 0.489 | 0.046 | 0.465 |
| | MEM0551 | 0.514 | 0.044 | 0.442 |
| | MEM0552 | 0.539 | 0.042 | 0.419 |
| | MEM0020 | 0.564 | 0.039 | 0.396 |
| | MEM0553 | 0.589 | 0.037 | 0.373 |
| | MEM0554 | 0.615 | 0.035 | 0.350 |
| | MEM0555 | 0.640 | 0.033 | 0.327 |
| | MEM0556 | 0.665 | 0.030 | 0.304 |
| | MEM0557 | 0.691 | 0.028 | 0.281 |
| | MEM0558 | 0.716 | 0.026 | 0.258 |
| | MEM0559 | 0.742 | 0.023 | 0.235 |
| | MEM0560 | 0.767 | 0.021 | 0.212 |
| | MEM0561 | 0.793 | 0.019 | 0.188 |
| | MEM0562 | 0.819 | 0.016 | 0.165 |
| | MEM0563 | 0.844 | 0.014 | 0.142 |
| | MEM0564 | 0.870 | 0.012 | 0.118 |
| | MEM0565 | 0.896 | 0.009 | 0.095 |
| | MEM0566 | 0.922 | 0.007 | 0.071 |
| | MEM0567 | 0.948 | 0.005 | 0.047 |
| | MEM0568 | 0.974 | 0.002 | 0.024 |

TABLE 58-continued

| | | MCT | | |
|---|---|---|---|---|
| T80:P | ID | Water | Oil | Surfactant |
| | MEM0008 | 0.592 | 0.075 | 0.333 |
| | MEM0569 | 0.642 | 0.065 | 0.292 |
| | MEM0570 | 0.795 | 0.038 | 0.168 |
| | MEM0571 | 0.820 | 0.033 | 0.147 |
| | MEM0572 | 0.846 | 0.028 | 0.126 |
| | MEM0573 | 0.871 | 0.024 | 0.105 |
| | MEM0574 | 0.897 | 0.019 | 0.084 |
| | MEM0575 | 0.923 | 0.014 | 0.063 |
| | MEM0576 | 0.948 | 0.009 | 0.042 |
| | MEM0577 | 0.974 | 0.005 | 0.021 |

TABLE 59

| | | MCT | | |
|---|---|---|---|---|
| T80:G | ID | Water | Oil | Surfactant |
| 1 to 1 | MEM0722 | 0.495 | 0.042 | 0.463 |
| | MEM0723 | 0.520 | 0.040 | 0.440 |
| | MEM0724 | 0.546 | 0.038 | 0.416 |
| | MEM0019 | 0.571 | 0.036 | 0.393 |
| | MEM0725 | 0.597 | 0.034 | 0.370 |
| | MEM0726 | 0.622 | 0.032 | 0.346 |
| | MEM0727 | 0.648 | 0.029 | 0.322 |
| | MEM0728 | 0.674 | 0.027 | 0.298 |
| | MEM0729 | 0.701 | 0.025 | 0.274 |
| | MEM0730 | 0.727 | 0.023 | 0.250 |
| | MEM0731 | 0.753 | 0.021 | 0.226 |
| | MEM0732 | 0.780 | 0.018 | 0.201 |
| | MEM0733 | 0.807 | 0.016 | 0.177 |
| | MEM0734 | 0.834 | 0.014 | 0.152 |
| | MEM0735 | 0.861 | 0.012 | 0.127 |
| | MEM0736 | 0.889 | 0.009 | 0.102 |
| | MEM0737 | 0.916 | 0.007 | 0.077 |
| | MEM0738 | 0.944 | 0.005 | 0.051 |
| | MEM0739 | 0.972 | 0.002 | 0.026 |

TABLE 60

| | | MCT | | |
|---|---|---|---|---|
| T80:G | ID | Water | Oil | Surfactant |
| 2 to 1 | MEM0740 | 0.476 | 0.045 | 0.479 |
| | MEM0741 | 0.501 | 0.043 | 0.456 |
| | MEM0742 | 0.526 | 0.041 | 0.433 |
| | MEM0743 | 0.552 | 0.039 | 0.410 |
| | MEM0744 | 0.577 | 0.036 | 0.387 |
| | MEM0745 | 0.603 | 0.034 | 0.363 |
| | MEM0746 | 0.628 | 0.032 | 0.340 |
| | MEM0747 | 0.654 | 0.030 | 0.316 |
| | MEM0748 | 0.680 | 0.028 | 0.293 |
| | MEM0749 | 0.706 | 0.025 | 0.269 |
| | MEM0750 | 0.732 | 0.023 | 0.245 |
| | MEM0751 | 0.758 | 0.021 | 0.221 |
| | MEM0752 | 0.784 | 0.019 | 0.197 |
| | MEM0753 | 0.811 | 0.016 | 0.173 |
| | MEM0754 | 0.838 | 0.014 | 0.149 |
| | MEM0755 | 0.864 | 0.012 | 0.124 |
| | MEM0756 | 0.891 | 0.009 | 0.100 |
| | MEM0757 | 0.918 | 0.007 | 0.075 |
| | MEM0758 | 0.945 | 0.005 | 0.050 |
| | MEM0759 | 0.973 | 0.002 | 0.025 |
| | MEM0760 | 0.866 | 0.023 | 0.111 |
| | MEM0761 | 0.893 | 0.019 | 0.089 |
| | MEM0762 | 0.919 | 0.014 | 0.067 |
| | MEM0763 | 0.946 | 0.009 | 0.044 |
| | MEM0764 | 0.973 | 0.005 | 0.022 |

TABLE 61

| | | MCT | | |
|---|---|---|---|---|
| T80:G | ID | Water | Oil | Surfactant |
| 3 to 1 | MEM0765 | 0.479 | 0.045 | 0.475 |
| | MEM0766 | 0.504 | 0.043 | 0.453 |
| | MEM0767 | 0.529 | 0.041 | 0.430 |
| | MEM0768 | 0.555 | 0.039 | 0.407 |
| | MEM0769 | 0.580 | 0.037 | 0.383 |
| | MEM0770 | 0.605 | 0.034 | 0.360 |
| | MEM0771 | 0.631 | 0.032 | 0.337 |
| | MEM0772 | 0.657 | 0.030 | 0.314 |
| | MEM0773 | 0.682 | 0.028 | 0.290 |
| | MEM0774 | 0.708 | 0.025 | 0.266 |
| | MEM0775 | 0.734 | 0.023 | 0.243 |
| | MEM0776 | 0.760 | 0.021 | 0.219 |
| | MEM0777 | 0.786 | 0.019 | 0.195 |
| | MEM0778 | 0.813 | 0.016 | 0.171 |
| | MEM0779 | 0.839 | 0.014 | 0.147 |
| | MEM0780 | 0.866 | 0.012 | 0.123 |
| | MEM0781 | 0.892 | 0.009 | 0.098 |
| | MEM0782 | 0.919 | 0.007 | 0.074 |
| | MEM0783 | 0.946 | 0.005 | 0.049 |
| | MEM0784 | 0.973 | 0.002 | 0.025 |
| | MEM0785 | 0.558 | 0.078 | 0.364 |
| | MEM0007 | 0.584 | 0.074 | 0.343 |
| | MEM0786 | 0.609 | 0.069 | 0.322 |
| | MEM0787 | 0.634 | 0.065 | 0.301 |
| | MEM0013 | 0.660 | 0.060 | 0.280 |
| | MEM0788 | 0.685 | 0.056 | 0.259 |
| | MEM0789 | 0.711 | 0.051 | 0.238 |
| | MEM0790 | 0.737 | 0.046 | 0.217 |
| | MEM0791 | 0.763 | 0.042 | 0.195 |
| | MEM0792 | 0.789 | 0.037 | 0.174 |
| | MEM0793 | 0.815 | 0.033 | 0.152 |
| | MEM0794 | 0.841 | 0.028 | 0.131 |
| | MEM0795 | 0.867 | 0.023 | 0.109 |
| | MEM0796 | 0.894 | 0.019 | 0.088 |
| | MEM0797 | 0.920 | 0.014 | 0.066 |
| | MEM0798 | 0.947 | 0.009 | 0.044 |
| | MEM0799 | 0.973 | 0.005 | 0.022 |

TABLE 62

| | | MCT | | |
|---|---|---|---|---|
| T80:G | ID | Water | Oil | Surfactant |
| 4 to 1 | MEM0800 | 0.481 | 0.045 | 0.473 |
| | MEM0801 | 0.506 | 0.043 | 0.451 |
| | MEM0802 | 0.531 | 0.041 | 0.428 |
| | MEM0803 | 0.556 | 0.039 | 0.405 |
| | MEM0804 | 0.582 | 0.037 | 0.382 |
| | MEM0805 | 0.607 | 0.034 | 0.358 |
| | MEM0806 | 0.633 | 0.032 | 0.335 |
| | MEM0807 | 0.658 | 0.030 | 0.312 |
| | MEM0808 | 0.684 | 0.028 | 0.288 |
| | MEM0809 | 0.710 | 0.025 | 0.265 |
| | MEM0810 | 0.736 | 0.023 | 0.241 |
| | MEM0811 | 0.762 | 0.021 | 0.218 |
| | MEM0812 | 0.788 | 0.019 | 0.194 |
| | MEM0813 | 0.814 | 0.016 | 0.170 |
| | MEM0814 | 0.840 | 0.014 | 0.146 |
| | MEM0815 | 0.867 | 0.012 | 0.122 |
| | MEM0816 | 0.893 | 0.009 | 0.098 |
| | MEM0817 | 0.920 | 0.007 | 0.073 |
| | MEM0818 | 0.946 | 0.005 | 0.049 |
| | MEM0819 | 0.973 | 0.002 | 0.025 |
| | MEM0039 | 0.560 | 0.078 | 0.362 |
| | MEM0820 | 0.585 | 0.074 | 0.341 |
| | MEM0821 | 0.610 | 0.069 | 0.320 |
| | MEM0822 | 0.636 | 0.065 | 0.299 |
| | MEM0823 | 0.661 | 0.060 | 0.278 |
| | MEM0040 | 0.687 | 0.056 | 0.257 |
| | MEM0824 | 0.713 | 0.051 | 0.236 |
| | MEM0825 | 0.738 | 0.047 | 0.215 |
| | MEM0826 | 0.764 | 0.042 | 0.194 |

TABLE 62-continued

| | | MCT | | |
|---|---|---|---|---|
| T80:G | ID | Water | Oil | Surfactant |
| | MEM0827 | 0.790 | 0.037 | 0.173 |
| | MEM0828 | 0.816 | 0.033 | 0.151 |
| | MEM0829 | 0.842 | 0.028 | 0.130 |
| | MEM0830 | 0.868 | 0.023 | 0.108 |
| | MEM0831 | 0.894 | 0.019 | 0.087 |
| | MEM0832 | 0.921 | 0.014 | 0.065 |
| | MEM0833 | 0.947 | 0.009 | 0.044 |
| | MEM0834 | 0.973 | 0.005 | 0.022 |

MEM0800-MEM0802 were unstable.

TABLE 63

| | | MCT | | |
|---|---|---|---|---|
| T80:G | ID | Water | Oil | Surfactant |
| 5 to 1 | MEM0835 | 0.482 | 0.046 | 0.472 |
| | MEM0836 | 0.507 | 0.043 | 0.449 |
| | MEM0837 | 0.532 | 0.041 | 0.426 |
| | MEM0838 | 0.558 | 0.039 | 0.403 |
| | MEM0839 | 0.583 | 0.037 | 0.380 |
| | MEM0840 | 0.608 | 0.034 | 0.357 |
| | MEM0841 | 0.634 | 0.032 | 0.334 |
| | MEM0842 | 0.659 | 0.030 | 0.311 |
| | MEM0843 | 0.685 | 0.028 | 0.287 |
| | MEM0844 | 0.711 | 0.025 | 0.264 |
| | MEM0845 | 0.736 | 0.023 | 0.240 |
| | MEM0846 | 0.762 | 0.021 | 0.217 |
| | MEM0847 | 0.788 | 0.019 | 0.193 |
| | MEM0848 | 0.815 | 0.016 | 0.169 |
| | MEM0849 | 0.841 | 0.014 | 0.145 |
| | MEM0850 | 0.867 | 0.012 | 0.121 |
| | MEM0851 | 0.893 | 0.009 | 0.097 |
| | MEM0852 | 0.920 | 0.007 | 0.073 |
| | MEM0853 | 0.947 | 0.005 | 0.049 |
| | MEM0854 | 0.973 | 0.002 | 0.024 |
| | MEM0855 | 0.561 | 0.078 | 0.361 |
| | MEM0856 | 0.586 | 0.074 | 0.340 |
| | MEM0857 | 0.611 | 0.069 | 0.319 |
| | MEM0858 | 0.637 | 0.065 | 0.298 |
| | MEM0859 | 0.662 | 0.060 | 0.277 |
| | MEM0860 | 0.688 | 0.056 | 0.256 |
| | MEM0861 | 0.713 | 0.051 | 0.235 |
| | MEM0862 | 0.739 | 0.047 | 0.214 |
| | MEM0863 | 0.765 | 0.042 | 0.193 |
| | MEM0864 | 0.791 | 0.037 | 0.172 |
| | MEM0865 | 0.817 | 0.033 | 0.151 |
| | MEM0866 | 0.843 | 0.028 | 0.129 |
| | MEM0867 | 0.869 | 0.023 | 0.108 |
| | MEM0868 | 0.895 | 0.019 | 0.086 |
| | MEM0869 | 0.921 | 0.014 | 0.065 |
| | MEM0870 | 0.947 | 0.009 | 0.043 |
| | MEM0871 | 0.974 | 0.005 | 0.022 |

MEM0835-MEM0838 were unstable.

TABLE 64

| | | MCT | | |
|---|---|---|---|---|
| T80:TriAc | ID | Water | Oil | Surfactant |
| 1 to 1 | MEM0947 | 0.478 | 0.045 | 0.477 |
| | MEM0948 | 0.503 | 0.043 | 0.454 |
| | MEM0949 | 0.528 | 0.041 | 0.431 |
| | MEM0021 | 0.553 | 0.039 | 0.408 |
| | MEM0950 | 0.579 | 0.036 | 0.385 |
| | MEM0951 | 0.604 | 0.034 | 0.361 |
| | MEM0952 | 0.630 | 0.032 | 0.338 |
| | MEM0953 | 0.656 | 0.030 | 0.315 |
| | MEM0954 | 0.681 | 0.028 | 0.291 |
| | MEM0955 | 0.707 | 0.025 | 0.267 |

TABLE 64-continued

MCT

| T80:TriAc | ID | Water | Oil | Surfactant |
|---|---|---|---|---|
| | MEM0956 | 0.733 | 0.023 | 0.244 |
| | MEM0957 | 0.759 | 0.021 | 0.220 |
| | MEM0958 | 0.786 | 0.019 | 0.196 |
| | MEM0959 | 0.812 | 0.016 | 0.172 |
| | MEM0960 | 0.839 | 0.014 | 0.148 |
| | MEM0961 | 0.865 | 0.012 | 0.123 |
| | MEM0962 | 0.892 | 0.009 | 0.099 |
| | MEM0963 | 0.919 | 0.007 | 0.074 |
| | MEM0964 | 0.946 | 0.005 | 0.050 |
| | MEM0965 | 0.973 | 0.002 | 0.025 |

TABLE 65

MCT

| T80:TriAc | ID | Water | Oil | Surfactant |
|---|---|---|---|---|
| 2 to 1 | MEM0966 | 0.482 | 0.046 | 0.473 |
| | MEM0009 | 0.507 | 0.043 | 0.450 |
| | MEM0967 | 0.532 | 0.041 | 0.427 |
| | MEM0015 | 0.557 | 0.039 | 0.404 |
| | MEM0968 | 0.582 | 0.037 | 0.381 |
| | MEM0969 | 0.608 | 0.034 | 0.358 |
| | MEM0970 | 0.633 | 0.032 | 0.335 |
| | MEM0971 | 0.659 | 0.030 | 0.311 |
| | MEM0972 | 0.684 | 0.028 | 0.288 |
| | MEM0973 | 0.710 | 0.025 | 0.265 |
| | MEM0974 | 0.736 | 0.023 | 0.241 |
| | MEM0975 | 0.762 | 0.021 | 0.217 |
| | MEM0976 | 0.788 | 0.019 | 0.193 |
| | MEM0977 | 0.893 | 0.009 | 0.097 |
| | MEM0978 | 0.920 | 0.007 | 0.073 |
| | MEM0979 | 0.946 | 0.005 | 0.049 |
| | MEM0980 | 0.973 | 0.002 | 0.025 |

TABLE 66

MCT

| T80:TriAc | ID | Water | Oil | Surfactant |
|---|---|---|---|---|
| 3 to 1 | MEM0981 | 0.483 | 0.046 | 0.471 |
| | MEM0982 | 0.508 | 0.043 | 0.448 |
| | MEM0983 | 0.533 | 0.041 | 0.425 |
| | MEM0984 | 0.559 | 0.039 | 0.402 |
| | MEM0985 | 0.584 | 0.037 | 0.379 |
| | MEM0986 | 0.609 | 0.035 | 0.356 |
| | MEM0987 | 0.635 | 0.032 | 0.333 |
| | MEM0988 | 0.660 | 0.030 | 0.310 |
| | MEM0989 | 0.686 | 0.028 | 0.287 |
| | MEM0990 | 0.711 | 0.026 | 0.263 |
| | MEM0991 | 0.737 | 0.023 | 0.240 |
| | MEM0992 | 0.920 | 0.007 | 0.073 |
| | MEM0993 | 0.947 | 0.005 | 0.049 |
| | MEM0994 | 0.973 | 0.002 | 0.024 |

TABLE 67

MCT

| T80:TriAc | ID | Water | Oil | Surfactant |
|---|---|---|---|---|
| 4 to 1 | MEM0995 | 0.484 | 0.046 | 0.470 |
| | MEM0996 | 0.509 | 0.044 | 0.447 |
| | MEM0997 | 0.534 | 0.041 | 0.424 |
| | MEM0998 | 0.559 | 0.039 | 0.401 |
| | MEM0999 | 0.585 | 0.037 | 0.378 |
| | MEM1000 | 0.610 | 0.035 | 0.355 |

TABLE 67-continued

MCT

| T80:TriAc | ID | Water | Oil | Surfactant |
|---|---|---|---|---|
| | MEM1001 | 0.635 | 0.032 | 0.332 |
| | MEM1002 | 0.661 | 0.030 | 0.309 |

TABLE 68

MCT

| T80:TriAc | ID | Water | Oil | Surfactant |
|---|---|---|---|---|
| 5 to 1 | MEM1003 | 0.485 | 0.046 | 0.469 |
| | MEM1004 | 0.510 | 0.044 | 0.447 |
| | MEM1005 | 0.535 | 0.041 | 0.424 |
| | MEM1006 | 0.560 | 0.039 | 0.401 |
| | MEM1007 | 0.636 | 0.032 | 0.332 |
| | MEM1008 | 0.662 | 0.030 | 0.308 |

Example 5

Comparison with Nanoemulsion

MSH-1001, a proprietary novel, highly insoluble small molecule, is an ATP-sensitive K channel opener that has been shown to reduce intraocular pressure.

Eleven different microemulsions and one nanoemulsion comprising varying specified amounts of MSH-1001 were prepared. Nanoemulsion ED-002 comprises 8 percent (w/w) castor oil, 2.2 percent (w/w) glycerin, 2 percent (w/w) Pluronic F68, 1 percent (w/w) soybean lecithin, 0.002 percent (w/w) alpha-tocopherol, and 85.8 percent (w/w) 1% carboxymethylcellulose (CMC)/deionized water. Compositions of the microemulsions used in this example are provided in Table 69.

TABLE 69

| ID | Surfactant | Co-Surfactant | % IPM | % Surfactant | MSH-1001 | Viscosity |
|---|---|---|---|---|---|---|
| ED-007 | 3:1 Crem | PG | 1.7 | 18.6 | 0.1% | 30.8 |
| ER-008 | 4:1 T80 | PG | 1.7 | 18.7 | 0.1% | 29.1 |
| ED-009 | 4:1 T80 | PG | 5.9 | 29.9 | 0.1% | 29.7 |
| ED-010 | 2:1 Crem | T20 | 1.7 | 19.3 | 0.1% | 28.2 |
| ED-011 | 3:1 Crem | T20 | 1.7 | 19.3 | 0.1% | 31.7 |
| ED-012 | 3:1 Crem | Triacetin | 1.4 | 18.6 | 0.1% | 28.9 |
| ED-013 | 3:1 Crem | Triacetin | 2.4 | 31.3 | 0.3% | 20.5 |
| ED-014 | 4:1 Crem | PG | 2.5 | 27.9 | 0.3% | 19.9 |
| ED-015 | 3:1 T80 | T20 | 3.0 | 39 | 0.3% | 458.9 |
| ED-016 | 3:1 Crem | PG | 2.5 | 27.8 | 0.3% | 15.6 |
| ED-017 | 3:1 Crem | PG | 3.3 | 37 | 0.3% | 185.7 |

Crem = cremophor;
PG = propylene glycol;
T20 = Tween 20;
T80 = Tween 80

Quantification of MSH-1001 in rabbit aqueous humor (AH) at 1 hour following administration of a single 60 μL eyedrop was performed using LC-MS/MS.

Figure 3:
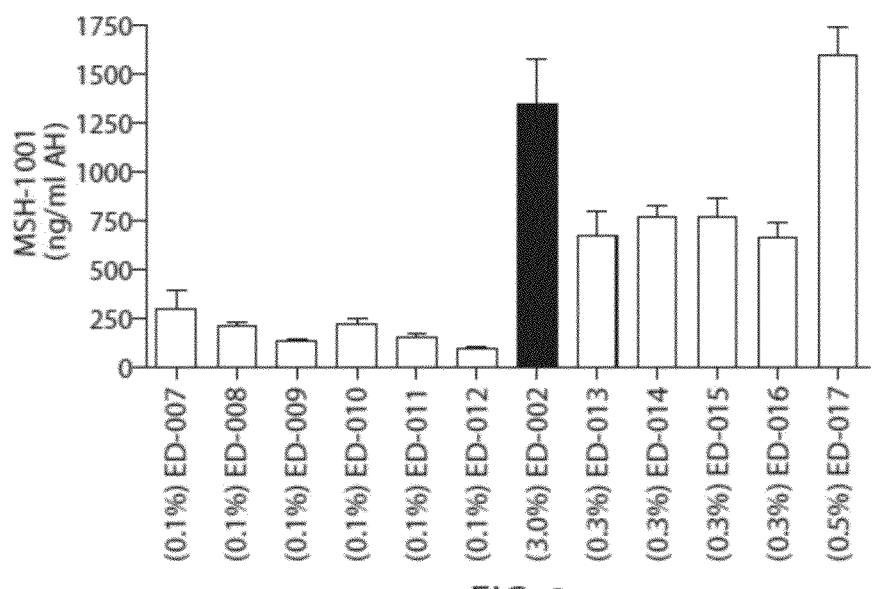
FIG. 3 is a graph depicting quantification of MSH-1001 in rabbit aqueous humor measured 1 hour after topical administration to the eye. X axis shows percent (w/v) of drug in individual emulsion formulations. ED-007 to ED-017 are microemulsions; ED-002 is a nanoemulsion. AH=aqueous humor; IPM=isopropyl myristate.

Representative results are shown in FIG. 3. Following topical administration of the various eyedrops it was observed that a 0.5% MSH-1001 microemulsion delivered the same drug levels to the aqueous humor as a 3% nanoemulsion and the 10% micronized suspension.

As shown in FIG. 3. MSH-1001 can be formulated into optically transparent and thermodynamically stable microemulsion eyedrops. These eyedrops, while having two orders of magnitude lower concentrations of the active ingredient, have demonstrated the ability to deliver the same concentration to the aqueous humor as more traditional eyedrop formulations. These results indicate that this microemulsion eyedrop formulation platform technology can be applied to increase ocular delivery of other lipophilic active pharmaceutical ingredients.

Example 6

Microemulsion Droplet Size

Figure 4:
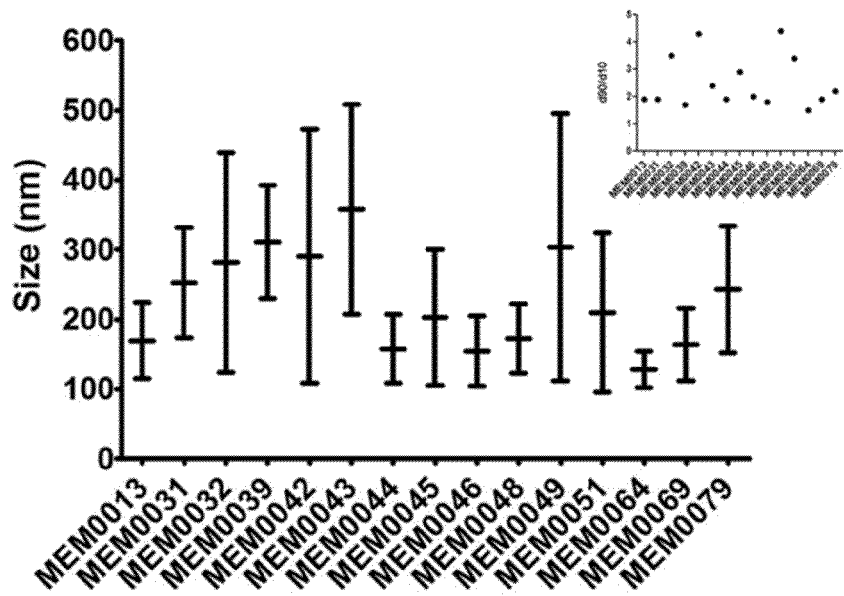
FIG. 4 is a whisker plot graph depicting microemulsion size distribution. Higher and lower extremes represent the d90 and d10 droplet sizes, respectively.
Figure 5:
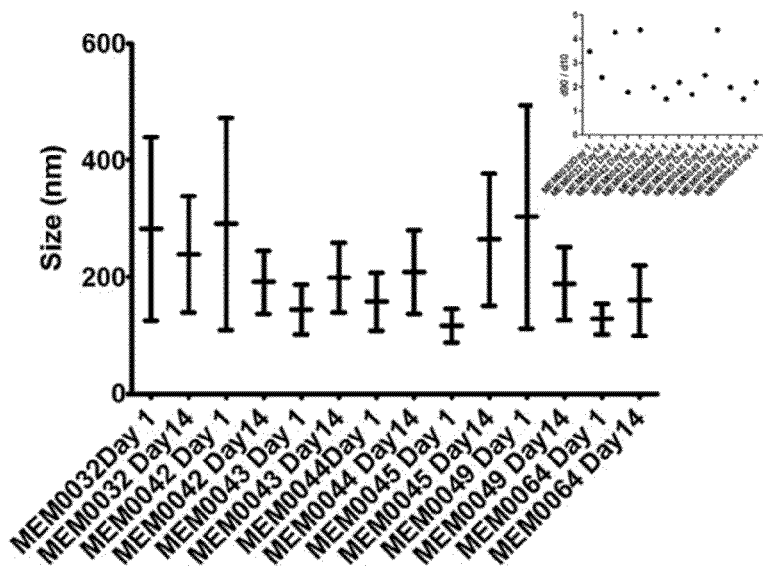
FIG. 5 is a whisker plot graph depicting microemulsion size distribution. Higher and lower extremes represent the d90 and d10 droplet sizes, respectively. Data is shown in pairs for values measured on Day 1 and Day 14 for each microemulsion.

Representative microemulsions were characterized in terms of droplet size of the emulsions. FIG. 4 shows the results of this analysis. The size distribution is plotted using a whisker plot, where the higher and lower extremes represent the d90 and d10 size distribution. D90 and d10 exclude the highest 10% and lowest 10% of the particle distribution, respectively. As can be observed from FIG. 4, there is variability in the d90 to d10 distribution. Most of the formulations tested had a d90:d10 ratio of about 2. The same can be said for the spread in FIG. 5, which is a comparison of the size of select formulations measured on day 1 and day 14.

Example 7

Microemulsion Formulations of Fenofibrate

In this example the ability of fenofibrate to form microemulsions in isopropyl myristate (IPM) was evaluated. Of 45 formulations of isopropyl myristate initially screened, 20 were identified that were compatible with 0.5% fenofibrate. Table 70 shows representative formulations made with IPM and Tween 80 (T80) as surfactant and propanediol (P) as co-surfactant. For comparison, formulations were also made with Tween 20 (T20) as the surfactant and Tween 80 (T80) as the co-surfactant. In this latter system 6 out of 15 screened formulations formed microemulsions with IPM (Table 71).

TABLE 70

Isopropyl Myristate (IPM) Microemulsions of 0.5% Fenofibrate

| MEM | Water | Oil IPM | Surfactant T80 | P |
|---|---|---|---|---|
| MEM0401 | 0.592 | 0.034 | 0.3000 | 0.0750 |
| MEM0402 | 0.617 | 0.031 | 0.2820 | 0.0704 |
| MEM0403 | 0.642 | 0.029 | 0.2620 | 0.0656 |
| MEM0409 | 0.592 | 0.034 | 0.3125 | 0.0625 |
| MEM0410 | 0.617 | 0.031 | 0.2933 | 0.0587 |
| MEM0381 | 0.492 | 0.042 | 0.3500 | 0.1165 |
| MEM0382 | 0.517 | 0.040 | 0.3320 | 0.1108 |
| MEM0383 | 0.542 | 0.038 | 0.3150 | 0.1050 |
| MEM0384 | 0.567 | 0.036 | 0.2980 | 0.0992 |
| MEM0385 | 0.592 | 0.034 | 0.2810 | 0.0935 |
| MEM0386 | 0.617 | 0.031 | 0.2630 | 0.0878 |
| MEM0387 | 0.642 | 0.029 | 0.2460 | 0.0820 |
| MEM0375 | 0.492 | 0.042 | 0.3110 | 0.1553 |
| MEM0376 | 0.517 | 0.040 | 0.2950 | 0.1477 |
| MEM0377 | 0.542 | 0.038 | 0.2800 | 0.1400 |

TABLE 71

Additional Isopropyl Myristate (IPM) Microemulsions of 0.5% Fenofibrate

| MEM | Water | Oil IPM | Surfactant T20 | T80 |
|---|---|---|---|---|
| MEM0042 | 0.498 | 0.038 | 0.232 | 0.232 |
| MEM0043 | 0.523 | 0.036 | 0.220 | 0.220 |
| MEM0044 | 0.548 | 0.035 | 0.209 | 0.209 |
| MEM0045 | 0.574 | 0.033 | 0.197 | 0.197 |
| MEM0053 | 0.687 | 0.025 | 0.057 | 0.230 |
| MEM0054 | 0.713 | 0.023 | 0.053 | 0.211 |

Example 8

Stability of Microemulsion Formulations of Fenofibrate

Figure 6:
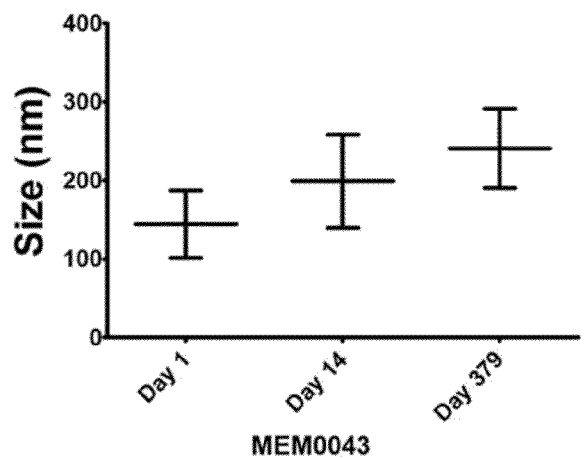
FIG. 6 is whisker plot graph depicting microemulsion size distribution for MEM0043 at Days 1, 14, and 379.

Microemulsion MEM0043 containing 0.5% fenofibrate was prepared as in Example 7 and stored at room temperature for over one year. Droplet size was assessed as in Example 6 on days 1, 14, and 379. Results are shown in FIG. 6. One-way ANOVA analysis showed there is no significant difference among the three groups (p>0.05).

Example 9

In Vivo Delivery of Fenofibrate and Fenofibric Acid to Mice

C57BL/6 mice were administered various formulations of fenofibrate via various routes of administration, and then ocular concentrations of fenofibrate and fenofibric acid were determined using LC/MS. For five consecutive days, fenofibrate drops were given QID in three different nanoemulsions NEM-001, NEM-002, and NEM-003 (each prepared with 0.5% and 3.0% fenofibrate); a UID oral administration at a concentration of 200 mg/kg; and three microemulsion formulations (MEM0043, MEM0044, and MEM0045) at 0.5% fenofibrate. Eyes were then enucleated and whole eye (pigmented epithelium, cornea, retina, sclera; aka PECRS) was homogenized and concentrations of fenofibrate and fenofibric acid were measured. Results of LC/MS measurements indicated that the three microemulsions delivered similar amounts of fenofibric acid, and more fenofibrate was measured with the 0.5% microemulsions compared to all three 0.5% nanoemulsions. The nanoemulsions exhibited significant creaming and are not considered to be stable for more than a week.

Example 10

In Vivo Delivery of Fenofibrate and Fenofibric Acid to Rats

Brown Norway rats were administered fenofibrate eye drops, either as a nanoemulsion (NEM-001) with 3% fenofibrate or as a microemulsion (MEM0043) with 0.5% fenofibrate, QID for 19 days. Eyes were then enucleated and the retina was separated from the PECS (pigmented epithelium, cornea, and sclera) and measured separately, as was the vitreous. PECS and retina were homogenized and concentrations of fenofibrate and fenofibric acid were measured using LC/MS. Results (Table 72) showed that the concentration of fenofibrate in both the retina and PECS was significantly higher with the 3% nanoemulsion than with the 0.5% microemulsion. However, the concentration of fenofibric acid was not significantly different between the two formulations as measured with Student's T test.

TABLE 72

LC/MS Quantification of Ocular Concentrations of Fenofibrate and Fenofibric Acid

| | | PECS | | Retina | | Vitreous | |
|---|---|---|---|---|---|---|---|
| ID | Treatment | Fenofibrate (ng/g) | Fenofibric Acid (ng/g) | Fenofibrate (ng/g) | Fenofibric Acid (ng/g) | Fenofibrate (ng/mL) | Fenofibric Acid (ng/L) |
| 1 | NEM-001 3.0% | 141.6 | 4.38 | 0.58 | 17.60 | 159.00 | 2.07 |
| 2 | NEM-001 3.0% | 3368.00 | 9.12 | 0.26 | 8.51 | 0.40 | 10.80 |
| 3 | NEM-001 3.0% | 72.8 | 4.17 | 0.31 | 2.93 | 0.67 | 0.76 |
| 4 | NEM-001 3.0% | 9.84 | 4.48 | 0.09 | 0.00 | 0.68 | 1.00 |
| 5 | NEM-001 3.0% | 3.70 | 10.56 | 457.71 | 3.84 | 0.39 | 1.55 |
| 6 | NEM-001 3.0% | 4.19 | 5.16 | 99.43 | 6.46 | 2.21 | 4.74 |
| 7 | NEM-001 3.0% | 3.07 | 4.66 | 18.11 | 3.54 | 0.77 | 0.71 |
| 8 | NEM-001 3.0% | 259.20 | 0.00 | 6.40 | 2.94 | 2.00 | 0.00 |
| 9 | MEM0043 0.5% | 2.21 | 0.00 | 2.37 | 4.37 | 0.52 | 2.80 |
| 10 | MEM0043 0.5% | 3.57 | 10.72 | 4.28 | 7.83 | 0.75 | 12.80 |
| 11 | MEM0043 0.5% | 4.62 | 0.00 | 1.27 | 7.83 | 0.70 | 0.61 |
| 12 | MEM0043 0.5% | 6.29 | 0.00 | 0.00 | 5.16 | 15.90 | 3.03 |
| 13 | MEM0043 0.5% | 34.32 | 0.00 | 6.51 | 7.09 | 0.33 | 8.99 |
| 14 | MEM0043 0.5% | 10.56 | 8.64 | 1.05 | 5.77 | 1440.00 | 6.53 |
| 15 | MEM0043 0.5% | 4.78 | 11.36 | 0.00 | 8.34 | 24.10 | 11.00 |
| 16 | MEM0043 0.5% | 6.15 | 13.68 | 2.23 | 8.63 | 2.06 | 3.83 |
| 17 | MEM0043 0.5% | 3.76 | 8.96 | 1.46 | 3.66 | 0.56 | 4.85 |
| 18 | MEM0043 0.5% | 5.34 | 4.34 | 1.14 | 2.82 | 0.11 | 0.50 |
| 19 | MEM0043 0.5% | 5.34 | 16.80 | 1.31 | 10.23 | 0.97 | 4.27 |
| 20 | MEM0043 0.5% | 31.60 | 11.92 | 0.47 | 12.29 | 0.43 | 1.51 |

Example 11

In Vivo Delivery of Fenofibrate and Fenofibric Acid to Rabbits

Figure 7:
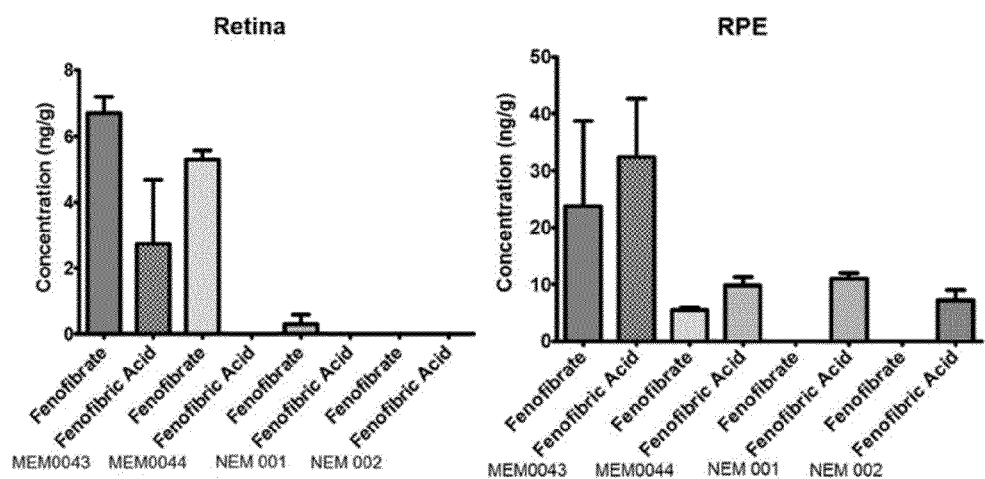
FIG. 7 is a pair of bar graphs depicting concentrations of fenobrate and fenofibric acid in retina (left panel) and retinal pigment epithelium (RPE) (right panel) of rabbits, as measured by LC/MS, following QID×5 days eye drop administration to eyes of fenofibrate formulated as 0.5% fenofibrate in the indicated microemulsions (MEM0043 and MEM0044) or 3% fenofibrate in the indicated nanoemulsions (NEM 001 and NEM 002).

Dutch belted rabbits were administered fenofibrate eye drops QID for 5 days. Two nanoemulsions (NEM-001 and NEM-002) with 3% fenofibrate and two microemulsion (MEM0043 and MEM0044) with 0.5% fenofibrate were administered for this study. Eyes were then enucleated and the tissue was dissected (retina, retinal pigment epithelium (RPE), vitreous humor, aqueous humor, sclera, iris, cornea, and conjunctiva). The tissues were homogenized and concentrations of fenofibrate and fenofibric acid were measured using LC/MS. Table 73 shows the results of these LC/MS measurements, and FIG. 7 shows the concentrations of fenofibrate and fenofibric acid in the retina and RPE for all four formulations. Surprisingly, in both of these posterior tissues the 0.5% microemulsions had higher drug concentration than the 3.0% nanoemulsions. In the retina there was virtually no fenofibrate or fenofibric acid in eyes that were dosed with either nanoemulsion. In eyes that were dosed with microemulsion, there were fairly consistent amounts of fenofibrate but very little fenofibric acid in the retina samples. In the RPE much higher concentration of fenofibric acid could be observed in all four formulations, while fenofibrate could not be detected at all in the nanoemulsions, and MEM0043 had higher fenofibrate and fenofibric acid than MEM0044. In the anterior corneal tissue large concentrations of fenofibric acid were detected in the microemulsion formulations, while the concentration of fenofibric acid measured in the nanoemulsion formulations was almost two orders of magnitude lower.

The results shown in FIG. 7 are surprising because they show very different drug dispositions within eye tissue depending on formulation, notwithstanding the similarity in particle size for the microemulsion formulations (137±40.3 nm) and the nanoemulsion formulations (205±74.9 nm).

TABLE 73

LC/MS Quantification of Ocular Concentrations of Fenofibrate and Fenofibric Acid

| | | | Tissue Type: | | | |
|---|---|---|---|---|---|---|
| | | | Retina | | RPE | |
| Animal Number | Treatment Group | Fenofibrate Concentration | Fenofibrate (ng/g) | Fenofibric Acid (ng/g) | Fenofibrate (ng/g) | Fenofibric Acid (ng/g) |
| 1154R | NEM001 | 3.0% | 0.00 | 0.00 | 0.00 | 12.30 |
| 1154L | NEM001 | 3.0% | 0.00 | 0.00 | 0.00 | 12.90 |

TABLE 73-continued

LC/MS Quantification of Ocular Concentrations of Fenofibrate and Fenofibric Acid

| | | | | | | |
|---|---|---|---|---|---|---|
| 1155R | NEM001 | 3.0% | 113.10 | 0.00 | 0.00 | 9.70 |
| 1155L | NEM001 | 3.0% | 0.90 | 0.00 | 0.00 | 9.30 |
| 1160R | NEM002 | 3.0% | 0.00 | 0.00 | 0.00 | 11.50 |
| 1160L | NEM002 | 3.0% | 0.00 | 0.00 | 0.00 | 3.00 |
| 1161R | NEM002 | 3.0% | 0.00 | 0.00 | 0.00 | 5.70 |
| 1161L | NEM002 | 3.0% | 0.00 | 0.00 | 0.00 | 8.70 |
| 1156R | MEM0043 | 0.5% | 8.20 | 2.80 | 1960.00 | 22.10 |
| 1156L | MEM0043 | 0.5% | 6.20 | 8.20 | 53.80 | 62.90 |
| 1157R | MEM0043 | 0.5% | 6.30 | 0.00 | 7.70 | 25.50 |
| 1157L | MEM0043 | 0.5% | 6.10 | 0.00 | 9.70 | 19.20 |
| 1158R | MEM0044 | 0.5% | 5.90 | 0.00 | 5.30 | 11.60 |
| 1158L | MEM0044 | 0.5% | 5.00 | 0.00 | 5.00 | 8.00 |
| 1159R | MEM0044 | 0.5% | 5.60 | 0.00 | 6.80 | 12.90 |
| 1159L | MEM0044 | 0.5% | 4.70 | 0.00 | 4.80 | 6.90 |

| | | | Tissue Type: | | | |
|---|---|---|---|---|---|---|
| | | | Vitreous | | Aqueous | |
| Animal Number | Treatment Group | Fenofibrate Concentration | Fenofibrate (ng/g) | Fenofibric Acid (ng/g) | Fenofibrate (ng/g) | Fenofibric Acid (ng/g) |
| 1154R | NEM001 | 3.0% | 0.00 | 0.00 | 0.00 | 5.53 |
| 1154L | NEM001 | 3.0% | 40.50 | 0.00 | 0.00 | 2.78 |
| 1155R | NEM001 | 3.0% | 0.00 | 0.00 | 0.00 | 2.15 |
| 1155L | NEM001 | 3.0% | 0.00 | 0.00 | 0.00 | 1.52 |
| 1160R | NEM002 | 3.0% | 0.00 | 0.00 | 0.00 | 5.14 |
| 1160L | NEM002 | 3.0% | 0.00 | 0.62 | 0.00 | 6.22 |
| 1161R | NEM002 | 3.0% | 0.00 | 0.00 | 0.00 | 3.56 |
| 1161L | NEM002 | 3.0% | 0.00 | 0.00 | 0.00 | 26.60 |
| 1156R | MEM0043 | 0.5% | 0.67 | 0.00 | 0.66 | 7.41 |
| 1156L | MEM0043 | 0.5% | 0.55 | 0.00 | 1.01 | 8.63 |
| 1157R | MEM0043 | 0.5% | 0.50 | 0.00 | 0.85 | 7.05 |
| 1157L | MEM0043 | 0.5% | 0.71 | 0.00 | 0.67 | 4.33 |
| 1158R | MEM0044 | 0.5% | 0.62 | 0.00 | 0.55 | 6.75 |
| 1158L | MEM0044 | 0.5% | 0.71 | 0.00 | 0.82 | 3.42 |
| 1159R | MEM0044 | 0.5% | 0.68 | 0.00 | 0.78 | 5.10 |
| 1159L | MEM0044 | 0.5% | 0.75 | 0.00 | 0.78 | 2.22 |

| | | | Tissue Type: | | | |
|---|---|---|---|---|---|---|
| | | | Sclera | | Iris | |
| Animal Number | Treatment Group | Fenofibrate Concentration | Fenofibrate (ng/g) | Fenofibric Acid (ng/g) | Fenofibrate (ng/g) | Fenofibric Acid (ng/g) |
| 1154R | NEM001 | 3.0% | 0.00 | 36.10 | 0.00 | 0.00 |
| 1154L | NEM001 | 3.0% | 0.00 | 19.00 | 0.00 | 0.00 |
| 1155R | NEM001 | 3.0% | 0.00 | 9.90 | 0.00 | 1.20 |
| 1155L | NEM001 | 3.0% | 0.00 | 21.50 | 0.00 | 2.70 |
| 1160R | NEM002 | 3.0% | 0.00 | 20.10 | 81.10 | 0.00 |
| 1160L | NEM002 | 3.0% | 0.00 | 25.10 | 0.00 | 0.00 |
| 1161R | NEM002 | 3.0% | 0.00 | 14.40 | 223.40 | 0.00 |
| 1161L | NEM002 | 3.0% | 0.00 | 9.60 | 0.00 | 0.00 |
| 1156R | MEM0043 | 0.5% | 35.70 | 81.70 | 273.10 | 164.60 |
| 1156L | MEM0043 | 0.5% | 25.90 | 92.60 | 13.80 | 30.30 |
| 1157R | MEM0043 | 0.5% | 16.20 | 73.70 | 13.70 | 0.70 |
| 1157L | MEM0043 | 0.5% | 41.10 | 56.90 | 4.50 | 2.40 |
| 1158R | MEM0044 | 0.5% | 6.90 | 54.70 | 4.70 | 0.40 |
| 1158L | MEM0044 | 0.5% | 9.00 | 54.50 | 3.40 | 0.00 |
| 1159R | MEM0044 | 0.5% | 21.60 | 80.60 | 2.80 | 1.20 |
| 1159L | MEM0044 | 0.5% | 15.50 | 72.00 | 3.10 | 1.20 |

| | | | Tissue Type: | | | |
|---|---|---|---|---|---|---|
| | | | Cornea | | Conjunctiva | |
| Animal Number | Treatment Group | Fenofibrate Concentration | Fenofibrate (ng/g) | Fenofibric Acid (ng/g) | Fenofibrate (ng/g) | Fenofibric Acid (ng/g) |
| 1154R | NEM001 | 3.0% | 0.00 | 256.60 | 0.20 | 161.10 |
| 1154L | NEM001 | 3.0% | 0.00 | 205.70 | 0.00 | 110.90 |
| 1155R | NEM001 | 3.0% | 0.00 | 76.60 | 0.00 | 49.10 |
| 1155L | NEM001 | 3.0% | 0.00 | 102.30 | 0.00 | 49.90 |
| 1160R | NEM002 | 3.0% | 0.00 | 98.30 | 0.00 | 85.10 |

TABLE 73-continued

LC/MS Quantification of Ocular Concentrations of Fenofibrate and Fenofibric Acid

| 1160L | NEM002 | 3.0% | 0.00 | 173.70 | 0.00 | 81.10 |
|---|---|---|---|---|---|---|
| 1161R | NEM002 | 3.0% | 0.00 | 113.70 | 0.00 | 42.30 |
| 1161L | NEM002 | 3.0% | 0.00 | 70.30 | 1931.40 | 23.10 |
| 1156R | MEM0043 | 0.5% | 5.30 | 7657.10 | 4.20 | 278.30 |
| 1156L | MEM0043 | 0.5% | 8.60 | 8857.10 | 7.40 | 282.90 |
| 1157R | MEM0043 | 0.5% | 7.80 | 8628.60 | 9.10 | 406.30 |
| 1157L | MEM0043 | 0.5% | 5.60 | 10685.70 | 4.00 | 242.90 |
| 1158R | MEM0044 | 0.5% | 4.80 | 10342.90 | 4.90 | 407.40 |
| 1158L | MEM0044 | 0.5% | 14.00 | 11714.30 | 4.30 | 278.90 |
| 1159R | MEM0044 | 0.5% | 12.90 | 15314.30 | 3.40 | 361.70 |
| 1159L | MEM0044 | 0.5% | 6.20 | 13257.10 | 6.70 | 258.90 |

Example 12

In Vivo Efficacy of Fenofibrate Microemulsion Formulation

Figure 8:
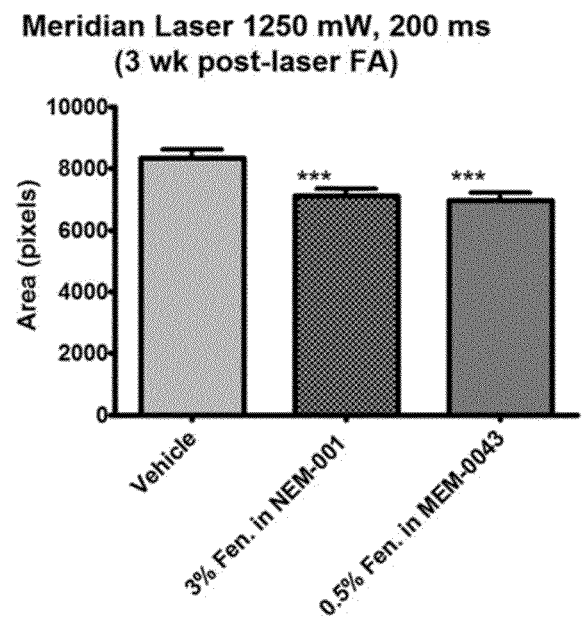
FIG. 8 is a bar graph depicting lesion size measured in rats where choroidal neovascularization was induced by laser. Rats were treated QID for 19 consecutive days with either vehicle alone or fenofibrate formulated as 3% fenofibrate in nanoemulsion (NEM-001) or 0.5% fenofibrate in microemulsion (MEM-0043). *** $p<0.001$ compared to vehicle.

To show that the levels of fenofibrate and fenofibric acid are therapeutically relevant we used a laser-induced choroidal neovascularization rodent model. The rats used in this study were the same animals used in Example 10. On Day 1, 3 subchoroidal neovascular lesions/wounds were created in both eyes of 8-week old female Brown Norway rats at the 3 o'clock, 6 o'clock, and 9 o'clock positions. On Day 2, cohorts of 5 rats were randomly assigned to treatment groups and received 25 μL eyedrop applications of 0.0% (vehicle), 0.5% MEM0043, or 3% NEM-001 Q.I.D. for 19 days. On Day 22, in vivo fluorescein angiography was performed on all rats utilizing intraperitoneal administration of fluorescein sodium and funduscope imaging coupled with a 488 nm bandpass filter. Both fluorescent and color funduscopic images were captured for each eye, and lesion areas were hand-quantified by masked observers. FIG. 8 shows representative results of the quantification of the leakage measurements. The leakage in both the nanoemulsion and the microemulsion formulations were significantly (p<0.001) reduced compared to vehicle.

Example 13

Synthesis of CLT-005

CLT-005 can be synthesized as shown in Scheme 1 or as shown in Scheme 2:

Scheme 1

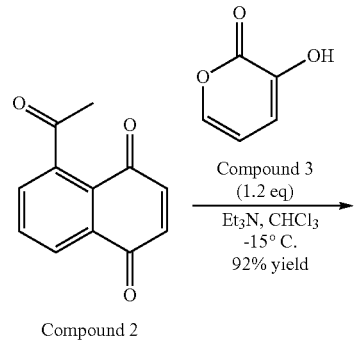

Compound 1

-continued

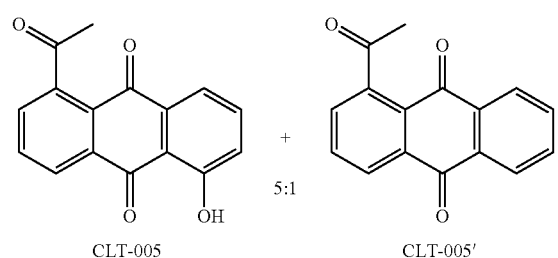

Scheme 2

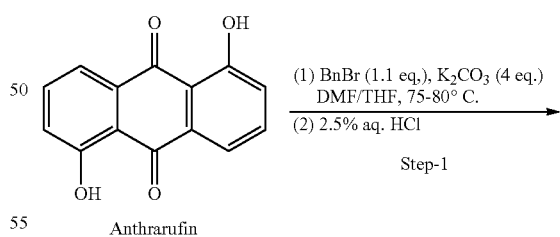

Anthrarufin

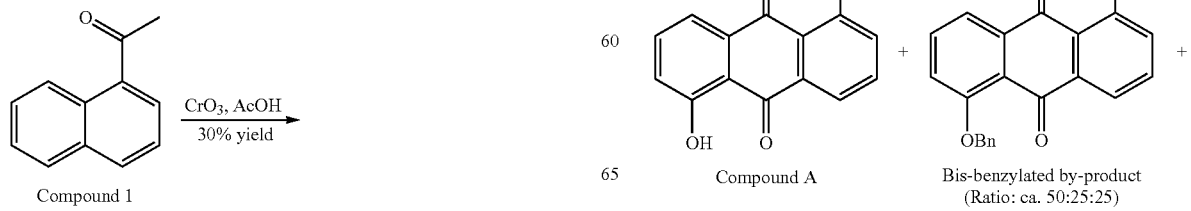

Compound A     Bis-benzylated by-product (Ratio: ca. 50:25:25)

-continued

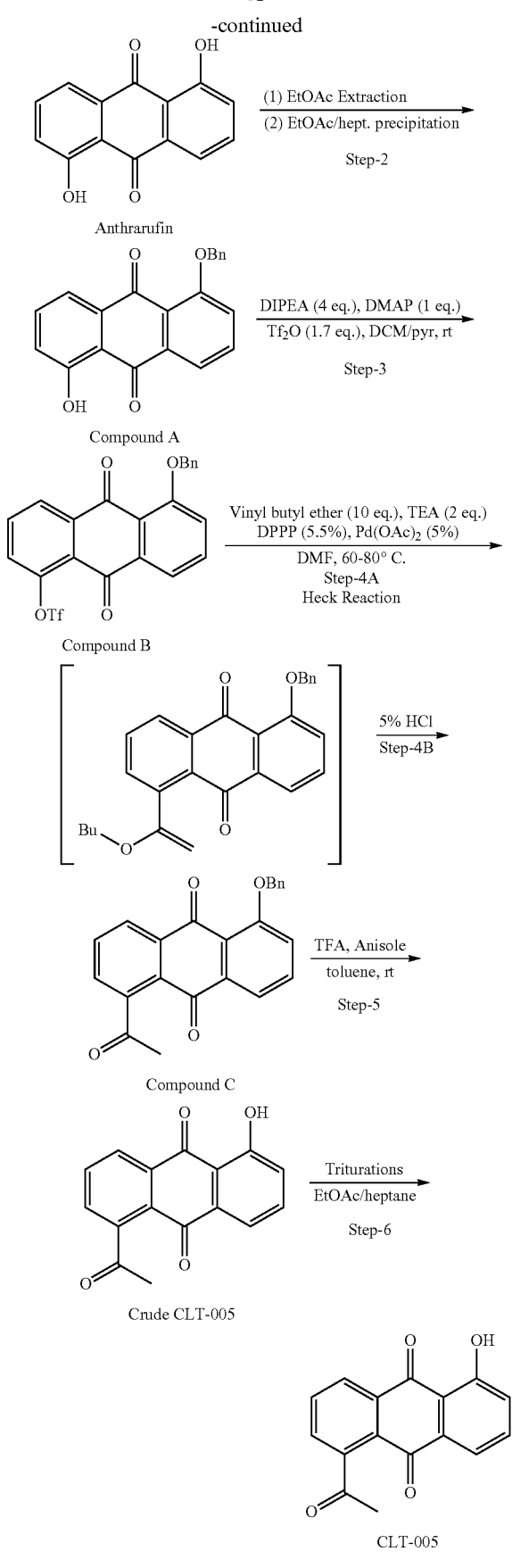

EQUIVALENTS

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

INCORPORATION BY REFERENCE

All patents and published patent applications mentioned in the description above are incorporated by reference herein in their entirety.

We claim:

1. A pharmaceutical carrier suitable for topical administration to the eye, comprising:
   an oil-in-water microemulsion comprising
   (i) an oil selected from the group consisting of isopropyl myristate, isopropyl palmitate, and medium chain triglycerides;
   (ii) a pair of surfactants selected from the group consisting of two polysorbates, a polysorbate and propylene glycol, a polysorbate and glycerol, a polysorbate and 1,2,3-triacetoxypropane, polyethoxylated castor oil and 1,2,3-triacetoxypropane, and polyethoxylated castor oil and propylene glycol; and
   (iii) water,
   wherein:
   the water represents 50 to about 95 percent (w/w) of the pharmaceutical carrier;
   the oil and the pair of surfactants represent substantially all of the remainder of the pharmaceutical carrier; and
   the ratio of percent (w/w) the pair of surfactants to percent (w/w) the oil is at least about 10:1.

2. The pharmaceutical carrier of claim 1, wherein the oil is isopropyl myristate.

3. The pharmaceutical carrier of claim 1, wherein the oil is isopropyl palmitate.

4. The pharmaceutical carrier of claim 1, wherein the oil is medium chain triglycerides.

5. The pharmaceutical carrier of claim 1, wherein the pair of surfactants is two polysorbates.

6. The pharmaceutical carrier of claim 1, wherein the pair of surfactants is a polysorbate and propylene glycol.

7. The pharmaceutical carrier of claim 1, wherein the pair of surfactants is a polysorbate and glycerol.

8. The pharmaceutical carrier of claim 1, wherein the pair of surfactants is a polysorbate and 1,2,3-triacetoxypropane.

9. The pharmaceutical carrier of claim 1, wherein the pair of surfactants is polyethoxylated castor oil and 1,2,3-triacetoxypropane.

10. The pharmaceutical carrier of claim 1, wherein the pair of surfactants is polyethoxylated castor oil and propylene glycol.

11. A method of making the pharmaceutical carrier of claim 1, comprising:
    combining the oil and the pair of surfactants, to yield an oil/surfactant mixture; and
    combining the oil/surfactant mixture with the water.

12. A pharmaceutical composition, comprising a lipophilic active pharmaceutical ingredient (API) and the pharmaceutical carrier of claim 1, wherein the pharmaceutical composition is formulated for topical administration to the eye.

13. The pharmaceutical composition of claim 12, wherein the lipophilic API is selected from the group consisting of anti-inflammatory agents, anti-infective agents, anti-allergic agents, antihistamines, antiproliferative agents, anti-angiogenic agents, anti-oxidants, antihypertensive agents, neuroprotective agents, cell receptor agonists, cell receptor antagonists, immunomodulating agents, immunosuppressive agents, intraocular pressure lowering agents, $\alpha 2$-adrenergic receptor agonists, $\beta 1$-adrenergic receptor antagonists, carbonic anhydrase inhibitors, cholinesterase inhibitor miotics, prostaglandins, prostaglandin receptor agonists, mast cell degranulation inhibitors, thromboxane A2 mimetics, protein kinase inhibitors, prostaglandin F derivatives, prostaglandin $F_{2\alpha}$ receptor antagonists, cyclooxygenase-2 inhibitors, muscarinic agents, and any combination thereof.

14. The pharmaceutical composition of claim 12, wherein the lipophilic API is selected from the group consisting of adaprolol maleate, cyclosporine A, fenofibrate, fenofibric acid, indomethacin, miconazole, pilocarpine, piroxicam, and $\Delta^8$-THC.

15. The pharmaceutical composition of claim 12, wherein the lipophilic API is fenofibrate.

16. The pharmaceutical composition of claim 12, wherein the lipophilic API is fenofibric acid.

17. The pharmaceutical composition of claim 12, wherein the pharmaceutical composition is formulated as eyedrops.

18. A method of making the pharmaceutical composition of claim 12, comprising:
    combining the oil, the pair of surfactants, and the lipophilic active pharmaceutical ingredient (API), to yield an oil/surfactant/API mixture; and
    combining the oil/surfactant/API mixture with the water.

19. A pharmaceutical composition, comprising an effective amount, for treating a disease of the posterior segment of the eye, of a compound represented by

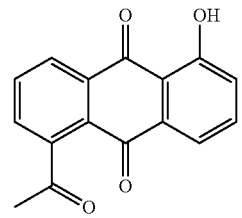 [SMILES: CC(=O)c1cccc2c1C(=O)c1cccc(O)c1C2=O]

and the pharmaceutical carrier of claim 1, wherein the pharmaceutical composition is formulated for topical administration to the eye.

20. The pharmaceutical composition of claim 19, wherein the pharmaceutical composition is formulated as eyedrops.

* * * * *